(12) United States Patent
Bialas et al.

(10) Patent No.: US 10,321,996 B2
(45) Date of Patent: Jun. 18, 2019

(54) PROSTHETIC VALVE DELIVERY APPARATUS HAVING CLUTCH MECHANISM

(71) Applicant: Edwards Lifesciences Corporation, Irvine, CA (US)

(72) Inventors: Michael R. Bialas, Lake Forest, CA (US); Asher L. Metchik, Newport Beach, CA (US)

(73) Assignee: Edwards Lifesciences Corporation, Irvine, CA (US)

(*) Notice: Subject to any disclaimer, the term of this patent is extended or adjusted under 35 U.S.C. 154(b) by 315 days.

(21) Appl. No.: 15/346,355

(22) Filed: Nov. 8, 2016

(65) Prior Publication Data

US 2017/0128197 A1      May 11, 2017

Related U.S. Application Data

(60) Provisional application No. 62/254,124, filed on Nov. 11, 2015.

(51) Int. Cl.
*A61F 2/24*      (2006.01)

(52) U.S. Cl.
CPC ............ *A61F 2/243* (2013.01); *A61F 2/2412* (2013.01); *A61F 2/2418* (2013.01); *A61F 2/2427* (2013.01); *A61F 2/2439* (2013.01)

(58) Field of Classification Search
CPC ...... A61F 2/243; A61F 2/2427; A61F 2/2436; A61F 2/95; A61F 2/962; A61F 2/966; A61F 2002/011; A61F 2002/9517; A61F 2002/9665

USPC ................................................ 623/1.11, 1.23
See application file for complete search history.

(56) References Cited

U.S. PATENT DOCUMENTS

| 519,297 A | 5/1894 | Bauer |
| 4,035,849 A | 7/1977 | Angell et al. |
| 4,592,340 A | 6/1986 | Boyles |
| 4,955,895 A | 9/1990 | Sugiyama et al. |

(Continued)

FOREIGN PATENT DOCUMENTS

| CA | 2767527 A1 | 1/2011 |
| DE | 19532846 A1 | 3/1997 |

(Continued)

*Primary Examiner* — Martin T Ton
(74) *Attorney, Agent, or Firm* — Hans P. Smith

(57) ABSTRACT

In a particular embodiment, the present disclosure provides a delivery apparatus for delivering a medical device. The delivery apparatus includes an elongated component with an engagement portion and a disengagement portion. Rotating the elongated component in a first rotational direction moves the travelling component along the engagement portion in a first axial direction. When the travelling component is located within the disengagement portion, continued rotation of the elongated component in the first rotational direction does not cause further movement of the travelling component in the first axial direction. A biasing member is located proximate the disengagement portion and urges the travelling component to reengage the engagement potion. The delivery apparatus can reduce or prevent damage to the delivery apparatus, or a patient with whom the delivery apparatus is used, by reducing or eliminating torque transfer from the travelling component to an end of the elongated component.

20 Claims, 17 Drawing Sheets

(56) References Cited

U.S. PATENT DOCUMENTS

| | | |
|---|---|---|
| 4,994,077 A | 2/1991 | Dobben |
| 5,059,177 A | 10/1991 | Towne et al. |
| 5,176,698 A | 1/1993 | Burns et al. |
| 5,192,297 A | 3/1993 | Hull |
| 5,266,073 A | 11/1993 | Wall |
| 5,325,845 A | 7/1994 | Adair |
| 5,358,496 A | 10/1994 | Ortiz et al. |
| 5,411,552 A | 5/1995 | Andersen et al. |
| 5,554,185 A | 9/1996 | Block et al. |
| 5,591,195 A | 1/1997 | Taheri et al. |
| 5,599,305 A | 2/1997 | Hermann et al. |
| 5,632,760 A | 5/1997 | Sheiban et al. |
| 5,639,274 A | 6/1997 | Fischell et al. |
| 5,728,068 A | 3/1998 | Leone et al. |
| 5,749,890 A | 5/1998 | Shaknovich |
| 5,782,809 A | 7/1998 | Umeno et al. |
| 5,824,044 A | 10/1998 | Quiachon et al. |
| 5,840,081 A | 11/1998 | Andersen et al. |
| 5,908,405 A | 6/1999 | Imran et al. |
| 5,916,147 A | 6/1999 | Boury |
| 5,961,536 A | 10/1999 | Mickley et al. |
| 5,968,068 A | 10/1999 | Dehdashtian et al. |
| 6,019,777 A | 2/2000 | MacKenzie |
| 6,027,510 A | 2/2000 | Alt |
| 6,033,381 A | 3/2000 | Kontos |
| 6,040,416 A | 3/2000 | Sekharipuram et al. |
| 6,143,016 A | 11/2000 | Bleam et al. |
| 6,162,208 A | 12/2000 | Hipps |
| 6,168,614 B1 | 1/2001 | Andersen et al. |
| 6,174,327 B1 | 1/2001 | Mertens et al. |
| 6,217,585 B1 | 4/2001 | Houser et al. |
| 6,235,050 B1 | 5/2001 | Quiachon et al. |
| 6,251,092 B1 | 6/2001 | Qin et al. |
| 6,379,372 B1 | 4/2002 | Dehdashtian et al. |
| 6,383,171 B1 | 5/2002 | Gifford et al. |
| 6,454,799 B1 | 9/2002 | Schreck |
| 6,458,153 B1 | 10/2002 | Bailey et al. |
| 6,461,382 B1 | 10/2002 | Cao |
| 6,471,672 B1 | 10/2002 | Brown et al. |
| 6,500,147 B2 | 12/2002 | Omaleki et al. |
| 6,514,228 B1 | 2/2003 | Hamilton et al. |
| 6,527,979 B2 | 3/2003 | Constantz et al. |
| 6,579,305 B1 | 6/2003 | Lashinski |
| 6,582,462 B1 | 6/2003 | Andersen et al. |
| 6,652,578 B2 | 11/2003 | Bailey et al. |
| 6,730,118 B2 | 5/2004 | Spenser et al. |
| 6,733,525 B2 | 5/2004 | Yang et al. |
| 6,764,504 B2 | 7/2004 | Wang et al. |
| 6,767,362 B2 | 7/2004 | Schreck |
| 6,830,584 B1 | 12/2004 | Seguin |
| 6,893,460 B2 | 5/2005 | Spenser et al. |
| 6,908,481 B2 | 6/2005 | Cribier |
| 7,011,094 B2 | 3/2006 | Rapacki et al. |
| 7,018,406 B2 | 3/2006 | Seguin et al. |
| 7,018,408 B2 | 3/2006 | Bailey et al. |
| 7,137,993 B2 | 11/2006 | Acosta et al. |
| 7,276,084 B2 | 10/2007 | Yang et al. |
| 7,318,278 B2 | 1/2008 | Zhang et al. |
| 7,320,702 B2 | 1/2008 | Hammersmark et al. |
| 7,320,704 B2 | 1/2008 | Lashinski et al. |
| 7,374,571 B2 | 5/2008 | Pease et al. |
| 7,393,360 B2 | 7/2008 | Spenser et al. |
| 7,435,257 B2 | 10/2008 | Lashinski et al. |
| 7,510,575 B2 | 3/2009 | Spenser et al. |
| 7,585,321 B2 | 9/2009 | Cribier |
| 7,594,926 B2 | 9/2009 | Linder et al. |
| 7,597,709 B2 | 10/2009 | Goodin |
| 7,618,446 B2 | 11/2009 | Andersen et al. |
| 7,749,266 B2 | 7/2010 | Forster et al. |
| 7,780,723 B2 | 8/2010 | Taylor |
| 7,780,726 B2 | 8/2010 | Seguin |
| 7,785,366 B2 | 8/2010 | Maurer et al. |
| 7,959,661 B2 | 6/2011 | Hijlkema et al. |
| 7,993,394 B2 | 8/2011 | Hariton et al. |
| 8,029,556 B2 | 10/2011 | Rowe |
| 8,167,932 B2 | 5/2012 | Bourang et al. |
| 8,182,530 B2 | 5/2012 | Huber |
| RE43,882 E | 12/2012 | Hopkins et al. |
| 8,449,606 B2 | 5/2013 | Eliasen et al. |
| 8,475,523 B2 | 7/2013 | Duffy |
| 8,568,472 B2 | 10/2013 | Marchand et al. |
| 8,652,145 B2 | 2/2014 | Maimon et al. |
| 8,652,202 B2 | 2/2014 | Alon et al. |
| 8,801,776 B2 | 8/2014 | House et al. |
| 9,061,119 B2 | 6/2015 | Le et al. |
| 9,119,716 B2 | 9/2015 | Lee et al. |
| 9,155,619 B2 | 10/2015 | Liu et al. |
| 9,168,131 B2 | 10/2015 | Yohanan et al. |
| 9,795,477 B2 | 10/2017 | Tran et al. |
| 9,867,700 B2 | 1/2018 | Bakis et al. |
| 2001/0002445 A1 | 5/2001 | Vesely |
| 2001/0007082 A1 | 7/2001 | Dusbabek et al. |
| 2002/0032481 A1 | 3/2002 | Gabbay |
| 2002/0058995 A1 | 5/2002 | Stevens |
| 2002/0161377 A1 | 10/2002 | Rabkin |
| 2002/0165461 A1 | 11/2002 | Hayzelden et al. |
| 2003/0040792 A1 | 2/2003 | Gabbay |
| 2003/0050694 A1 | 3/2003 | Yang et al. |
| 2003/0120341 A1 | 6/2003 | Shennib et al. |
| 2004/0093061 A1 | 5/2004 | Acosta et al. |
| 2004/0111095 A1 | 6/2004 | Gordon et al. |
| 2004/0133263 A1 | 7/2004 | Dusbabek et al. |
| 2004/0143197 A1 | 7/2004 | Soukup et al. |
| 2004/0186563 A1 | 9/2004 | Lobbi |
| 2004/0186565 A1 | 9/2004 | Schreck |
| 2004/0210304 A1 | 10/2004 | Seguin et al. |
| 2004/0236411 A1 | 11/2004 | Sarac et al. |
| 2004/0260389 A1 | 12/2004 | Case et al. |
| 2005/0075731 A1 | 4/2005 | Artof et al. |
| 2005/0080474 A1 | 4/2005 | Andreas et al. |
| 2005/0096736 A1 | 5/2005 | Osse et al. |
| 2005/0113910 A1 | 5/2005 | Paniagua et al. |
| 2005/0137688 A1 | 6/2005 | Salahieh et al. |
| 2005/0137689 A1 | 6/2005 | Salahieh et al. |
| 2005/0137693 A1 | 6/2005 | Haug et al. |
| 2005/0137697 A1 | 6/2005 | Salahieh et al. |
| 2005/0149159 A1 | 7/2005 | Andreas et al. |
| 2005/0149160 A1 | 7/2005 | McFerran |
| 2005/0203614 A1 | 9/2005 | Forster et al. |
| 2005/0203617 A1 | 9/2005 | Forster et al. |
| 2005/0245894 A1 | 11/2005 | Zadno-Azizi |
| 2006/0025857 A1 | 2/2006 | Bergheim et al. |
| 2006/0149360 A1 | 7/2006 | Schwammenthal et al. |
| 2006/0259136 A1 | 11/2006 | Nguyen et al. |
| 2006/0276813 A1 | 12/2006 | Greenberg |
| 2006/0282150 A1 | 12/2006 | Olson et al. |
| 2006/0287719 A1 | 12/2006 | Rowe et al. |
| 2007/0005131 A1 | 1/2007 | Taylor |
| 2007/0073389 A1 | 3/2007 | Bolduc et al. |
| 2007/0088431 A1 | 4/2007 | Bourang et al. |
| 2007/0112422 A1 | 5/2007 | Dehdashtian |
| 2007/0203575 A1 | 8/2007 | Forster et al. |
| 2007/0213813 A1 | 9/2007 | Von Segesser et al. |
| 2007/0219612 A1 | 9/2007 | Andreas et al. |
| 2007/0239254 A1 | 10/2007 | Chia et al. |
| 2007/0244546 A1 | 10/2007 | Francis |
| 2007/0265700 A1 | 11/2007 | Eliasen et al. |
| 2008/0065011 A1 | 3/2008 | Marchand et al. |
| 2008/0125853 A1 | 5/2008 | Bailey et al. |
| 2008/0294230 A1 | 11/2008 | Parker |
| 2008/0319526 A1 | 12/2008 | Hill et al. |
| 2009/0024428 A1 | 1/2009 | Hudock, Jr. |
| 2009/0069889 A1 | 3/2009 | Suri et al. |
| 2009/0099638 A1 | 4/2009 | Grewe |
| 2009/0138079 A1 | 5/2009 | Tuval et al. |
| 2009/0157175 A1 | 6/2009 | Benichou |
| 2009/0192585 A1 | 7/2009 | Bloom et al. |
| 2009/0228093 A1 | 9/2009 | Taylor et al. |
| 2009/0276040 A1 | 11/2009 | Rowe et al. |
| 2009/0281619 A1 | 11/2009 | Le et al. |
| 2009/0299456 A1 | 12/2009 | Melsheimer |
| 2009/0319037 A1 | 12/2009 | Rowe et al. |
| 2010/0030255 A1* | 2/2010 | Berra ............... A61F 2/07 606/200 |

(56) References Cited

U.S. PATENT DOCUMENTS

| | | |
|---|---|---|
| 2010/0030318 A1 | 2/2010 | Berra |
| 2010/0036472 A1 | 2/2010 | Papp |
| 2010/0036473 A1 | 2/2010 | Roth |
| 2010/0049313 A1 | 2/2010 | Alon et al. |
| 2010/0076402 A1 | 3/2010 | Mazzone et al. |
| 2010/0076541 A1 | 3/2010 | Kumoyama |
| 2010/0082089 A1 | 4/2010 | Quadri et al. |
| 2010/0094394 A1 | 4/2010 | Beach et al. |
| 2010/0121425 A1 | 5/2010 | Shimada |
| 2010/0145431 A1 | 6/2010 | Wu et al. |
| 2010/0161036 A1 | 6/2010 | Pintor et al. |
| 2010/0174363 A1 | 7/2010 | Castro |
| 2010/0191326 A1 | 7/2010 | Alkhatib |
| 2010/0198347 A1 | 8/2010 | Zakay et al. |
| 2010/0274344 A1 | 10/2010 | Dusbabek et al. |
| 2011/0015729 A1 | 1/2011 | Jimenez et al. |
| 2011/0040374 A1 | 2/2011 | Goetz et al. |
| 2011/0054596 A1 | 3/2011 | Taylor |
| 2011/0137331 A1 | 6/2011 | Walsh et al. |
| 2011/0160846 A1 | 6/2011 | Bishop et al. |
| 2011/0282424 A1 | 11/2011 | De La Rama et al. |
| 2012/0071969 A1 | 3/2012 | Li et al. |
| 2012/0123529 A1 | 5/2012 | Levi et al. |
| 2012/0221091 A1 | 8/2012 | Hartly et al. |
| 2012/0239142 A1 | 9/2012 | Liu et al. |
| 2013/0030519 A1 | 1/2013 | Tran et al. |
| 2013/0317598 A1 | 11/2013 | Rowe et al. |
| 2014/0243960 A1 | 8/2014 | Czyscon et al. |
| 2014/0296962 A1 | 10/2014 | Cartledge et al. |
| 2014/0343670 A1 | 11/2014 | Bakis et al. |
| 2015/0157455 A1 | 6/2015 | Hoang et al. |
| 2017/0056149 A1 | 3/2017 | Rajpara et al. |
| 2017/0065415 A1 | 3/2017 | Rupp et al. |
| 2017/0156839 A1 | 6/2017 | Cooper et al. |
| 2017/0156859 A1 | 6/2017 | Chang et al. |
| 2017/0231765 A1 | 8/2017 | Desrosiers et al. |
| 2017/0258584 A1 | 9/2017 | Chang et al. |
| 2018/0153689 A1 | 6/2018 | Maimon et al. |
| 2018/0344456 A1 | 12/2018 | Barash et al. |

FOREIGN PATENT DOCUMENTS

| | | |
|---|---|---|
| DE | 19907646 A1 | 8/2000 |
| EP | 0592410 A1 | 4/1994 |
| EP | 0850607 A1 | 7/1998 |
| EP | 1796597 A2 | 6/2007 |
| EP | 2218403 A1 | 8/2010 |
| FR | 2815844 A1 | 5/2002 |
| WO | 9117720 A1 | 11/1991 |
| WO | 9829057 A1 | 7/1998 |
| WO | 9912483 A1 | 3/1999 |
| WO | 0149213 A2 | 7/2001 |
| WO | 0154625 A1 | 8/2001 |
| WO | 0176510 A2 | 10/2001 |
| WO | 0222054 A1 | 3/2002 |
| WO | 0236048 A1 | 5/2002 |
| WO | 0247575 A2 | 6/2002 |
| WO | 02060352 | 8/2002 |
| WO | 03030776 A2 | 4/2003 |
| WO | 03047468 A1 | 6/2003 |
| WO | 2004019825 A1 | 3/2004 |
| WO | 2005084595 A1 | 9/2005 |
| WO | 05/102015 | 11/2005 |
| WO | 2006032051 A2 | 3/2006 |
| WO | 06/111391 | 10/2006 |
| WO | 06/138173 | 12/2006 |
| WO | 2007047488 A2 | 4/2007 |
| WO | 2007067942 A1 | 6/2007 |
| WO | 2008124844 A1 | 10/2008 |
| WO | 2010121076 A2 | 10/2010 |

* cited by examiner

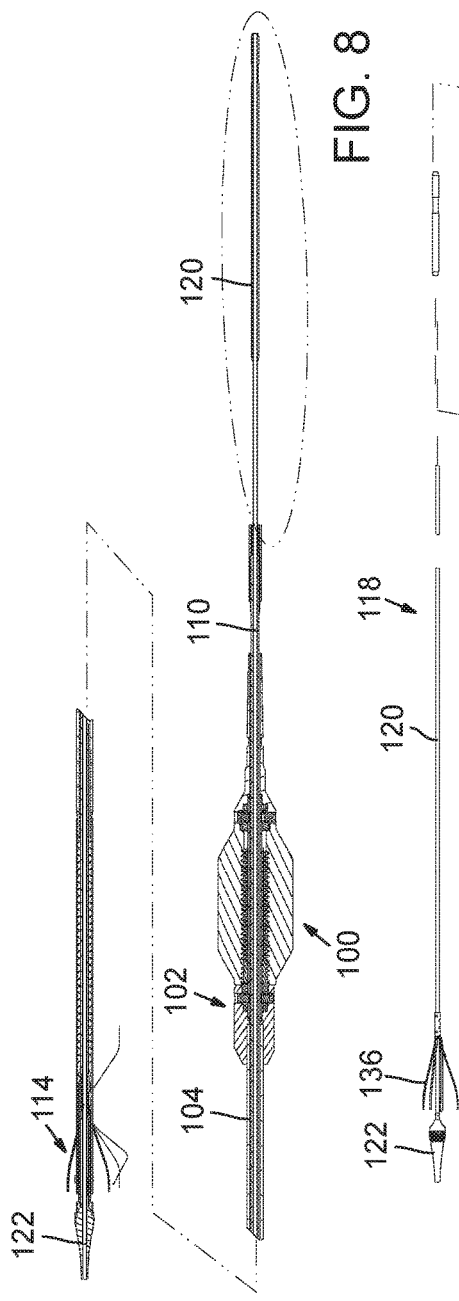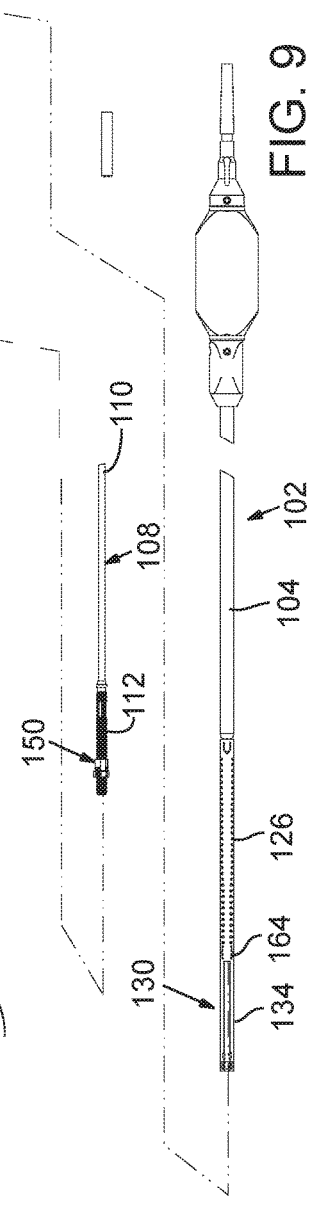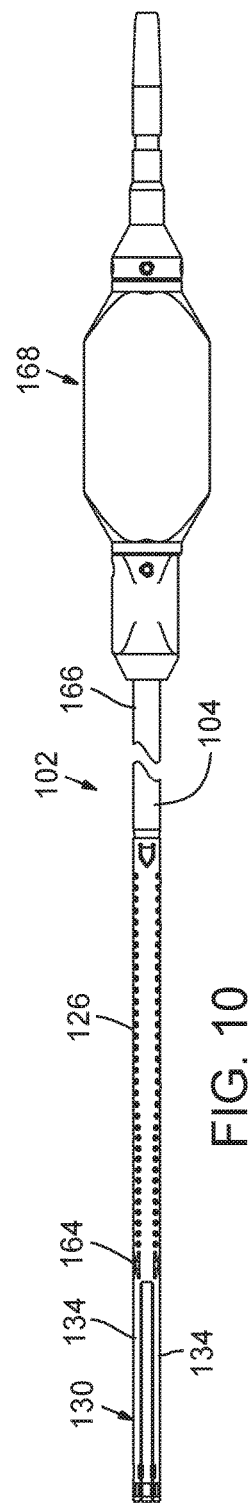

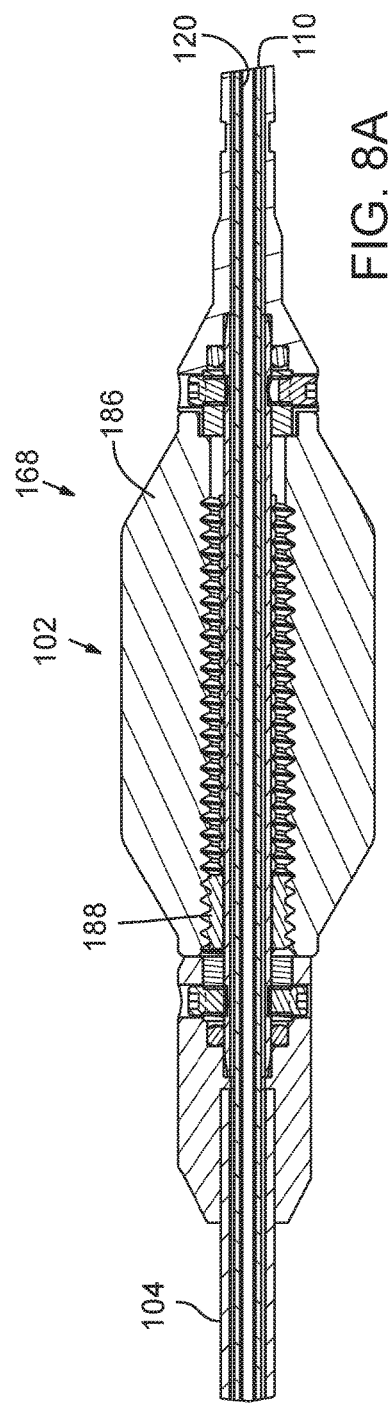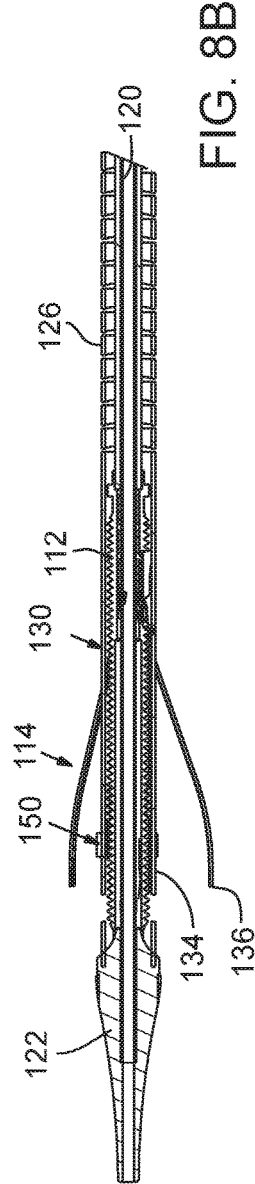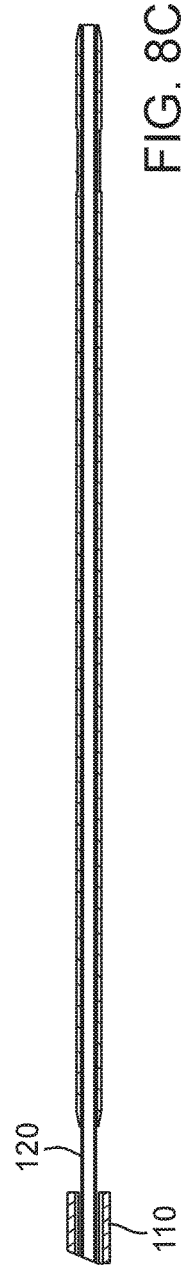

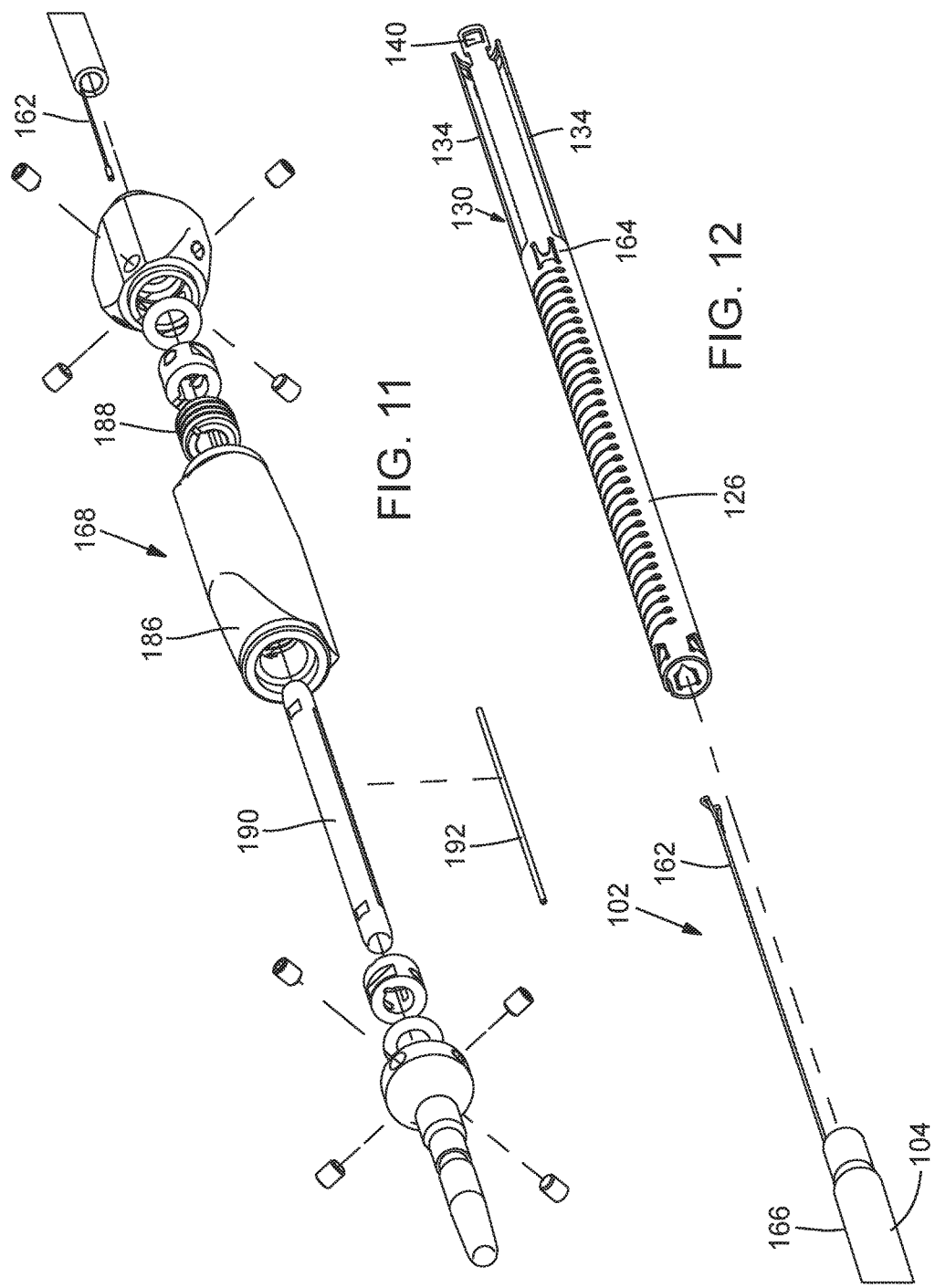

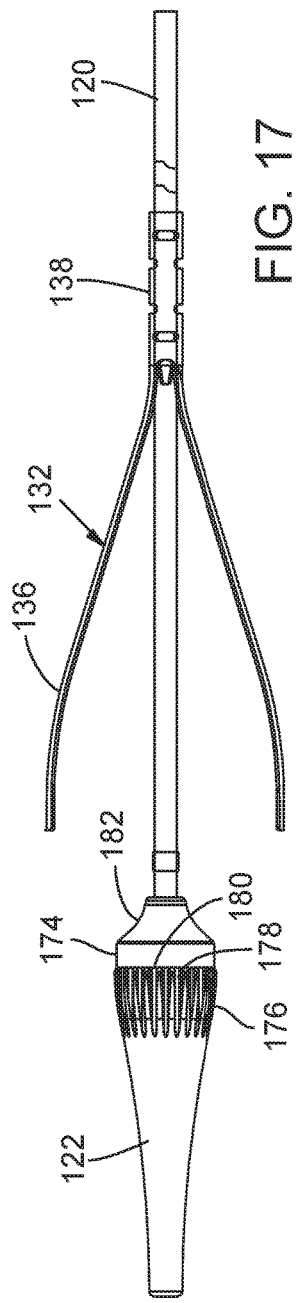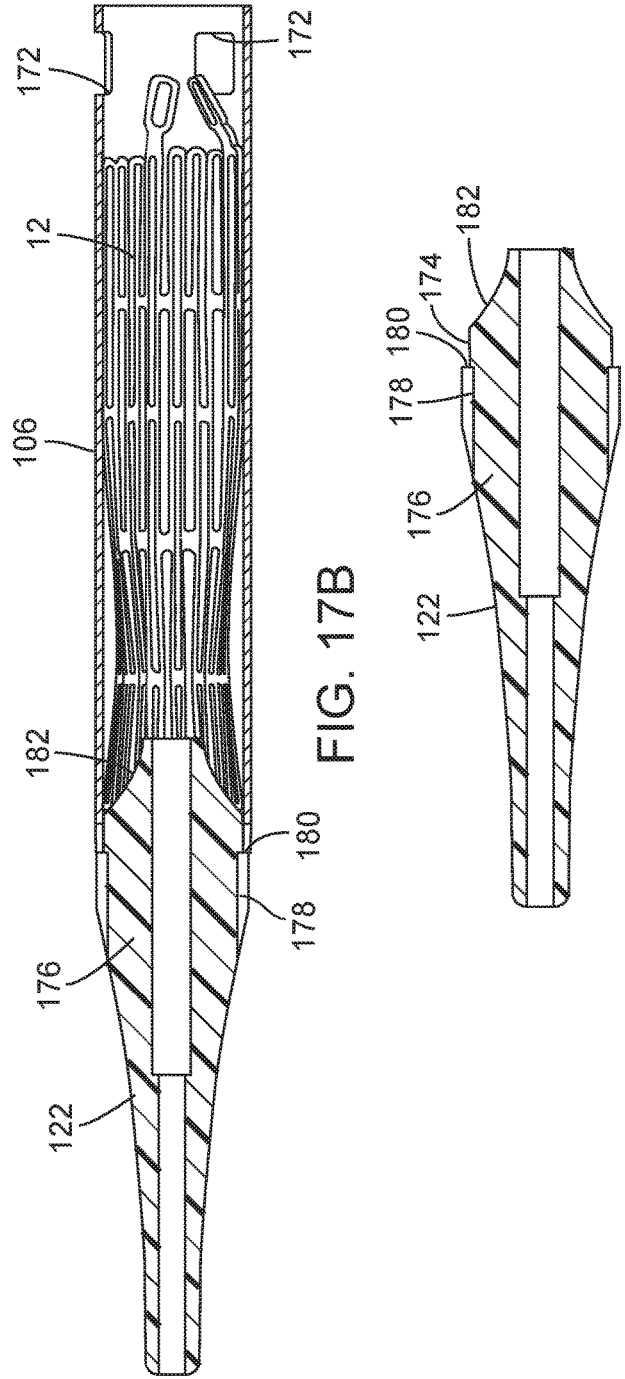

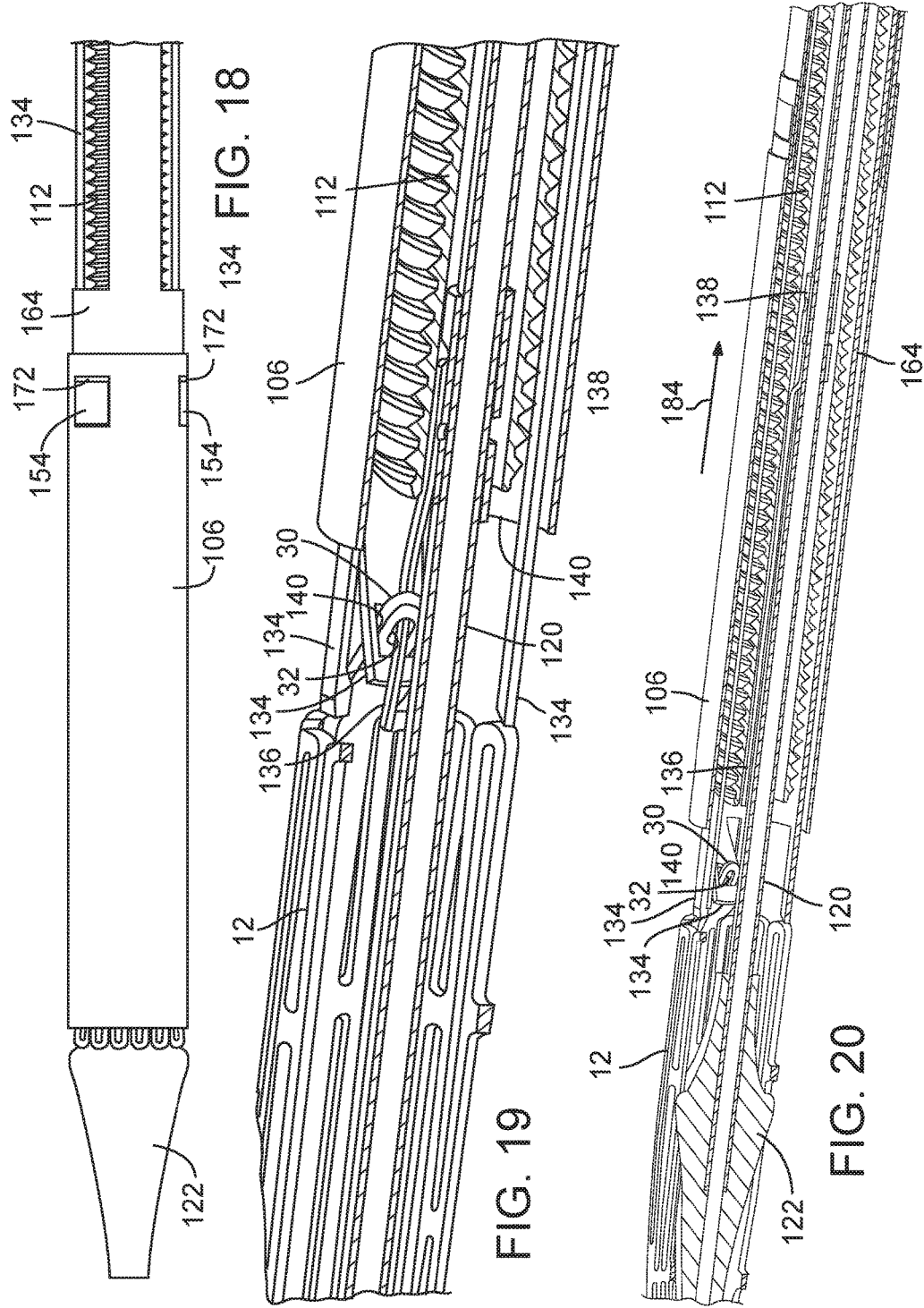

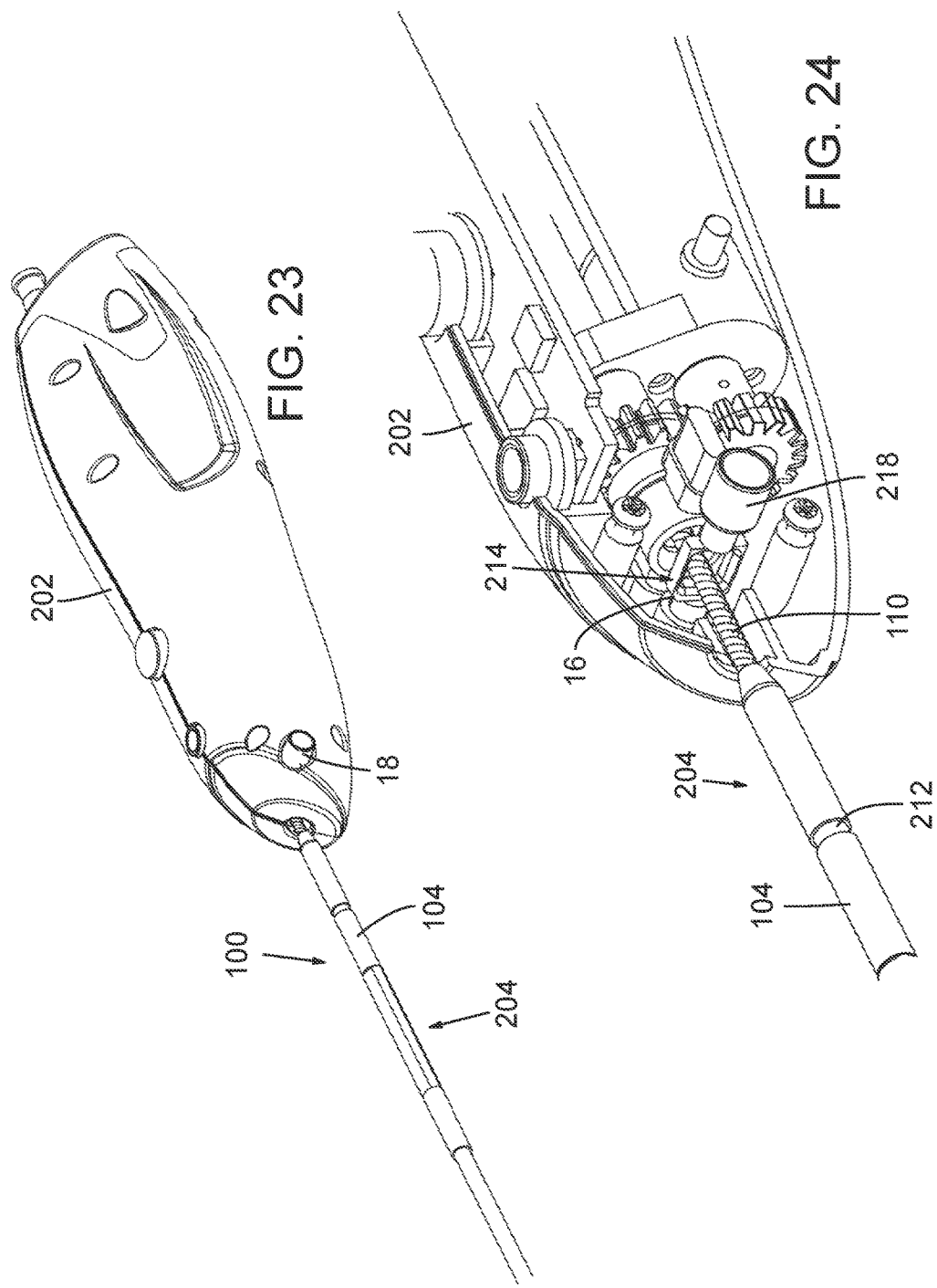

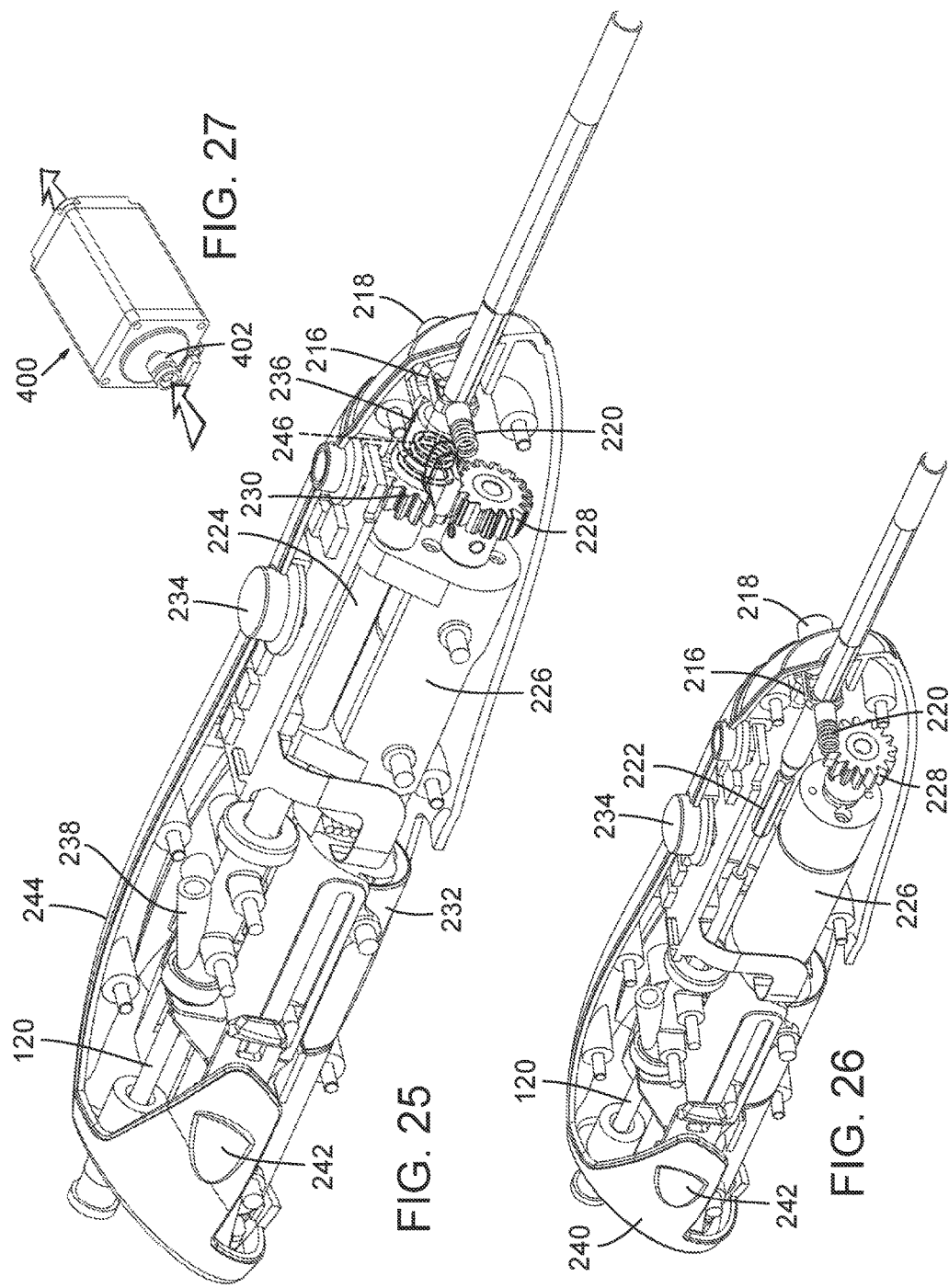

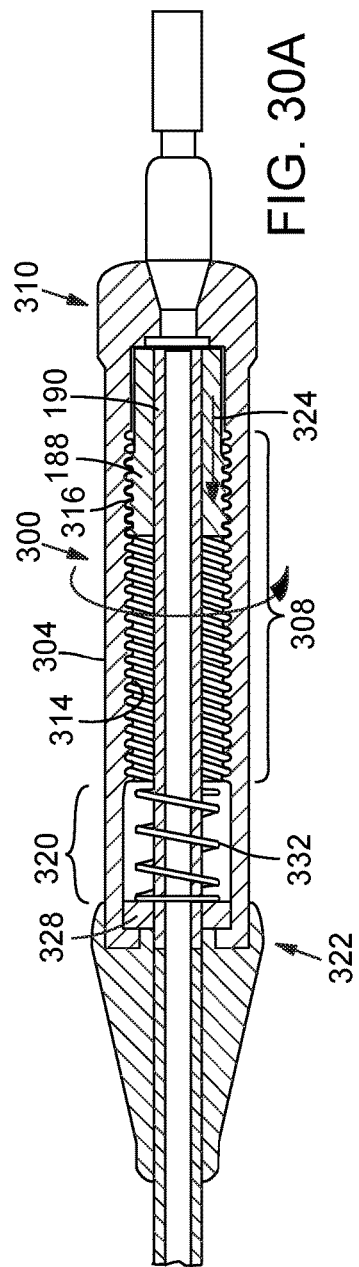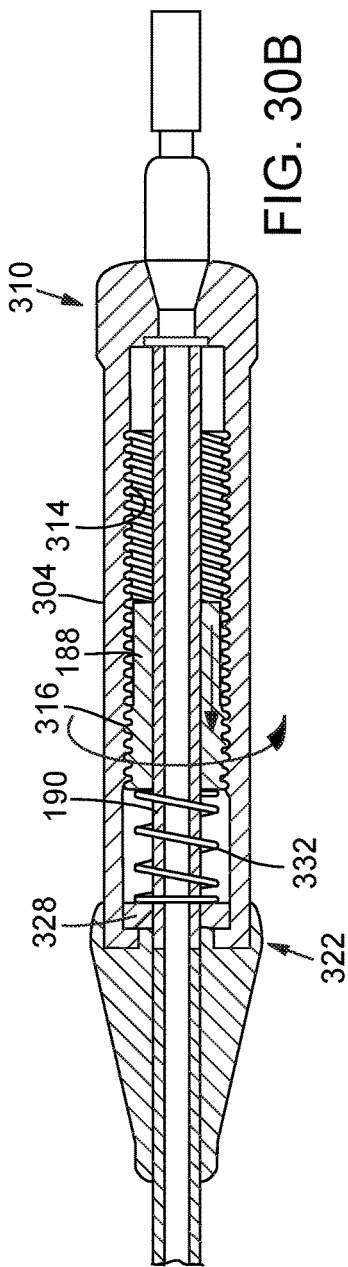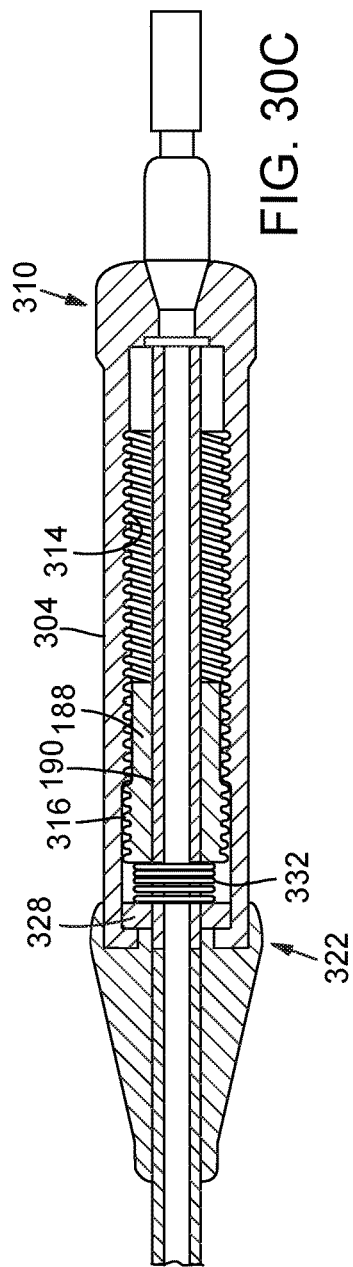

PROSTHETIC VALVE DELIVERY APPARATUS HAVING CLUTCH MECHANISM

CROSS REFERENCE TO RELATED APPLICATION

This application claims the benefit of, and incorporates by reference, U.S. Provisional Patent Application Ser. No. 62/254,124, filed Nov. 11, 2015.

FIELD

The present disclosure relates generally to moving a travelling component axially along an elongated component upon rotation of the elongated component. Particular implementations relate to elongated components having a disengagement portion for receiving the travelling component and, when so received, continued rotation of the elongated component in a first rotational direction does not result in further axial movement of the travelling component in a first axial direction.

BACKGROUND

Prosthetic cardiac valves have been used for many years to treat cardiac valvular disorders. The native heart valves (such as the aortic, pulmonary, and mitral valves) serve critical functions in assuring the forward flow of an adequate supply of blood through the cardiovascular system. These heart valves can be rendered less effective by congenital, inflammatory, or infectious conditions. Such damage to the valves can result in serious cardiovascular compromise or death. For many years, the definitive treatment for such disorders was the surgical repair or replacement of the valve during open heart surgery, but such surgeries are prone to many complications. More recently a transvascular technique has been developed for introducing and implanting a prosthetic heart valve using a flexible catheter in a manner that is less invasive than open heart surgery.

In this technique, a prosthetic valve is mounted in a crimped state on the end portion of a flexible catheter and advanced through a blood vessel of the patient until the prosthetic valve reaches the implantation site. The prosthetic valve at the catheter tip is then expanded to its functional size at the site of the defective native valve, such as by inflating a balloon on which the prosthetic valve is mounted. Alternatively, the prosthetic valve can have a resilient, self-expanding stent or frame that expands the prosthetic valve to its functional size when it is advanced from a delivery sheath at the distal end of the catheter.

Balloon-expandable prosthetic valves typically are preferred for replacing calcified native valves because the catheter balloon can apply sufficient expanding force to anchor the frame of the prosthetic valve to the surrounding calcified tissue. On the other hand, self-expanding prosthetic valves sometimes are preferred for replacing a defective, non-stenotic (non-calcified) native valve, although they also can be used to replace stenotic valves.

Because the catheter must be directed through a patient's vasculature, it typically is beneficial for the operator to be able to precisely control the operation of the catheter, including mechanisms that allow the catheter to be bent to assist in navigating the vasculature, and mechanisms that control deployment of the prosthetic valve.

SUMMARY

In various aspects, the present disclosure provides a clutch mechanism that causes a travelling component to engage an elongated component. A travelling component is a component that moves axially along the elongated component in first and second directions when the elongated components is rotated, respectively, in first or second directions. When the travelling component is engaged with the elongated component, rotation of the elongated component in the first rotational direction causes the travelling component to move axially along the elongated component in a first axial direction. When the travelling component is disengaged from the elongated component, continued rotation of the elongated component in the first rotational direction does not cause further axial movement of the travelling component in the first axial direction. When the elongated component is rotated in the second rotational direction, the clutch mechanism facilitates reengagement of the travelling component with the elongated component such that rotation of the elongated component in first and second directions again results in axial movement of the travelling component in, respectively, first or second axial directions.

Certain embodiments of the present disclosure incorporate a clutch mechanism in a delivery apparatus for a medical device. The delivery apparatus can include an elongated, first component having an engagement portion having threads or grooves and a disengagement portion lacking the threads or grooves. The delivery apparatus can further include a travelling component coaxially disposed relative to the first elongated component. The travelling component can include threads or grooves for engaging the threads or grooves of the first elongated component. In specific examples, the travelling component is a threaded nut, ring, or sleeve. The disengagement portion, in some implementations, has a length that is equal to or greater than the length of a threaded or grooved portion of the travelling component, such as a length that is at least the length of the travelling component.

In particular implementations, the delivery apparatus includes a biasing member located proximate the disengagement portion of the first elongated component. The biasing member, in a more particular implementation, is a spring. In further implementations, the biasing member, such as the spring, is selected to provide audible or tactile feedback to a user when the biasing member is sufficiently compressed by the travelling component, such as when the traveling component is located in the disengagement portion.

The first elongated component is configured to be rotatable relative to the traveling component such that rotation of the first elongated component in a first rotational direction causes the travelling component to move axially along the threads or grooves of the engagement portion in a first axial direction. When the travelling component moves into the disengagement portion, it disengages from the threads or grooves of the engagement portion. Further rotation of the first elongated component in the first rotational direction does not cause further axial movement of the travelling component in the first axial direction. When present, the biasing member biases the traveling component against the threads or grooves of the engagement potion such that, upon reversing the rotational direction of the first elongated component, the travelling component is urged by the biasing member to reengage the engagement portion.

By allowing the travelling component to disengage from the first elongated component, continued rotation of the first elongated component does not continue to axially move the travelling component along the length of the first elongated component, where it could abut and apply undue stress to components located at an end of the first elongated component. Similarly, the ability of the travelling component to disengage from the first elongated shaft can help prevent the travelling component from causing the delivery apparatus to twist, as it might if the torque from the travelling component were transmitted to components at an end of the first elongated component.

In particular implementations, the engagement portion and the disengagement portion are formed on an inner surface of the first elongated component. In some examples, the delivery apparatus includes a pull wire coupled to the travelling component. The pull wire may be further coupled to a distal end portion of a shaft of the delivery apparatus. Axial movement of the travelling component along the first elongated component causes the distal end portion of the shaft to deflect or return to a pre-deflected position, depending on the direction of axial movement.

In another implementation, the engagement portion and the disengagement portion are formed on an outer surface of the first elongated component. The delivery apparatus, in some examples, includes a delivery sheath configured to receive and retain a prosthetic valve in a compressed delivery state. The sheath is coupled to the travelling component. Rotation of the first elongated component causes the delivery sheath to advance or retract relative to the prosthetic valve when the travelling component is located on the engagement portion, depending on the direction of rotation.

In another aspect, the disengagement portion is a first disengagement portion located at a first end of the first elongated component and the first elongated component includes a second disengagement portion located at a second end of the first elongated component. In a particular implementation, the biasing member is a first biasing member located at the first end of the first elongated component and the delivery apparatus includes a second biasing member located at the second end of first elongated component.

In other embodiments, the present disclosure provides a method that includes inserting the distal end of an elongated delivery apparatus into the vasculature of a patient. The elongated delivery apparatus can include an elongated component having an engagement portion that includes threads or grooves and a disengagement portion lacking the threads or grooves. The elongated component is rotated in a first rotational direction to move a travelling component axially along the engagement portion of the elongated component in a first axial direction. The travelling component is axially moved into the disengagement portion of the elongated component. Continued rotation of the elongated component in the first rotational direction does not cause the travelling component to continue to move axially in the first axial direction. When the rotational direction of the elongated component is reversed, the travelling component reengages the engagement portion of the elongated component and moves axially along the elongated component in a second axial direction. In a particular example, when in the disengagement portion, the travelling component is biased, such as by compressing a spring, to facilitate reengagement of the travelling component with the engagement portion of the elongated component.

In one implementation, rotating the elongated component causes deflection of a portion of a distal end of the elongated delivery apparatus. For example, the travelling component may pull a pull wire coupled to a distal portion of the travelling component. In another implementation, the elongated delivery apparatus includes a delivery sheath containing a prosthetic valve in a radially compressed state. Rotating the elongated component causes the delivery sheath to move relative to the prosthetic valve.

In further implementations, the method includes providing tactile or audible feedback to a user when the travelling component is moved within the disengagement portion of the elongated component. In a particular example, the tactile or audible feedback is provided by a biasing member, such as a spring selected to have a suitable spring constant.

There are additional features and advantages of the various embodiments of the present disclosure. They will become evident from the following disclosure.

In this regard, it is to be understood that this is a summary of the various embodiments described herein. Any given embodiment of the present disclosure need not provide all features noted above, nor must it solve all problems or address all issues in the prior art noted above.

BRIEF DESCRIPTION OF THE DRAWINGS

Various embodiments are shown and described in connection with the following drawings in which:

FIG. 8 is a cross-sectional view of an embodiment of a delivery apparatus that can be used to deliver and implant a prosthetic valve, such as the prosthetic valve shown in FIG. 1.

FIGS. 8A-8C are enlarged cross-sectional views of sections of FIG. 8.

FIG. 9 is an exploded view of the delivery apparatus of FIG. 8.

FIG. 10 is a side view of the guide catheter of the delivery apparatus of FIG. 8.

FIG. 11 is a perspective, exploded view of the proximal end portion of the guide catheter of FIG. 10.

FIG. 12 is a perspective, exploded view of the distal end portion of the guide catheter of FIG. 10.

FIG. 17 is an enlarged side view of the distal end portion of the nose cone catheter of the delivery apparatus of FIG. 8.

FIG. 17A is an enlarged, cross-sectional view of the nose cone of the nose cone catheter shown FIG. 17.

FIG. 17B is an enlarged cross-sectional view of the distal end portion of the delivery apparatus of FIG. 8 showing the stent of a prosthetic valve retained in a compressed state within a delivery sheath.

FIG. 18 is an enlarged side view of the distal end portion of the delivery apparatus of FIG. 8 showing the delivery sheath in a delivery position covering a prosthetic valve in a compressed state for delivery into a patient.

FIG. 19 is an enlarged cross-sectional view of a section of the distal end portion of the delivery apparatus of FIG. 8 showing the valve-retaining mechanism securing the stent of a prosthetic valve to the delivery apparatus.

FIG. 20 is an enlarged cross-sectional view similar to FIG. 19, showing the inner fork of the valve-retaining mechanism in a release position for releasing the prosthetic valve from the delivery apparatus.

FIGS. 23-26 are various views of an embodiment of a motorized delivery apparatus that can be used to operate the torque shaft of the delivery apparatus shown in FIG. 8.

FIG. 27 is a perspective view of an alternative motor that can be used to operate the torque shaft of the delivery apparatus shown in FIG. 8.

FIGS. 30A-30C are enlarged, cross-sectional views of an alternative implementation of a flex control mechanism useable in the guide catheter of FIG. 11.

DETAILED DESCRIPTION

Figure 1:
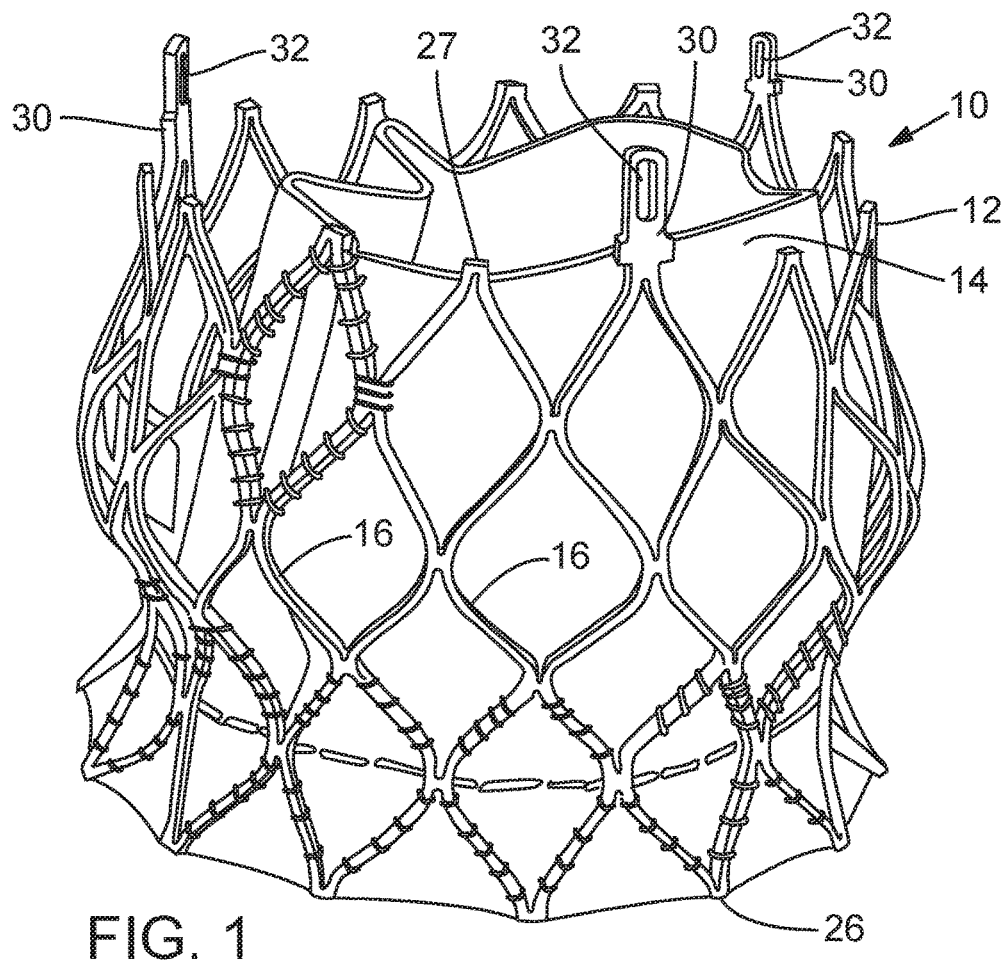
FIG. 1 is a perspective view of a prosthetic valve that can be used to replace the native aortic valve of the heart, according to one embodiment.

Referring first to FIG. 1, there is shown a prosthetic aortic heart valve 10, according to one embodiment. The prosthetic valve 10 includes an expandable frame member, or stent, 12 that supports a flexible leaflet section 14. The prosthetic valve 10 is radially compressible to a compressed state for delivery through the body to a deployment site and expandable to its functional size shown in FIG. 1 at the deployment site. In certain embodiments, the prosthetic valve 10 is self-expanding; that is, the prosthetic valve can radially expand to its functional size when advanced from the distal end of a delivery sheath. Apparatuses particularly suited for percutaneous delivery and implantation of a self-expanding prosthetic valve are described in detail below. In other embodiments, the prosthetic valve can be a balloon-expandable prosthetic valve that can be adapted to be mounted in a compressed state on the balloon of a delivery catheter. The prosthetic valve can be expanded to its functional size at a deployment site by inflating the balloon, as known in the art.

The illustrated prosthetic valve 10 is adapted to be deployed in the native aortic annulus, although it also can be used to replace the other native valves of the heart. Moreover, the prosthetic valve 10 can be adapted to replace other valves within the body, such venous valves.

Figure 3:
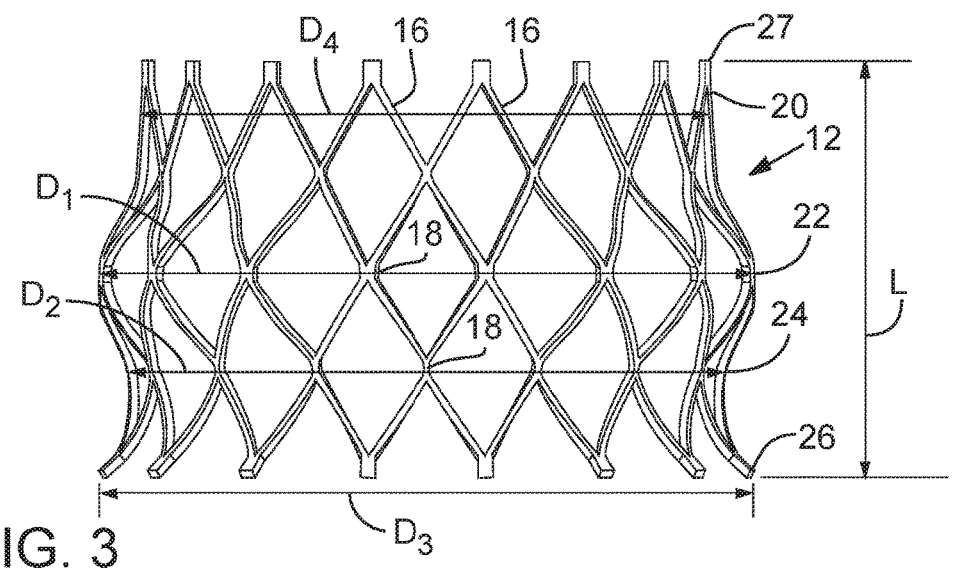
FIG. 3 is side elevation view of the support frame of the prosthetic valve of FIG. 1.
Figure 4:
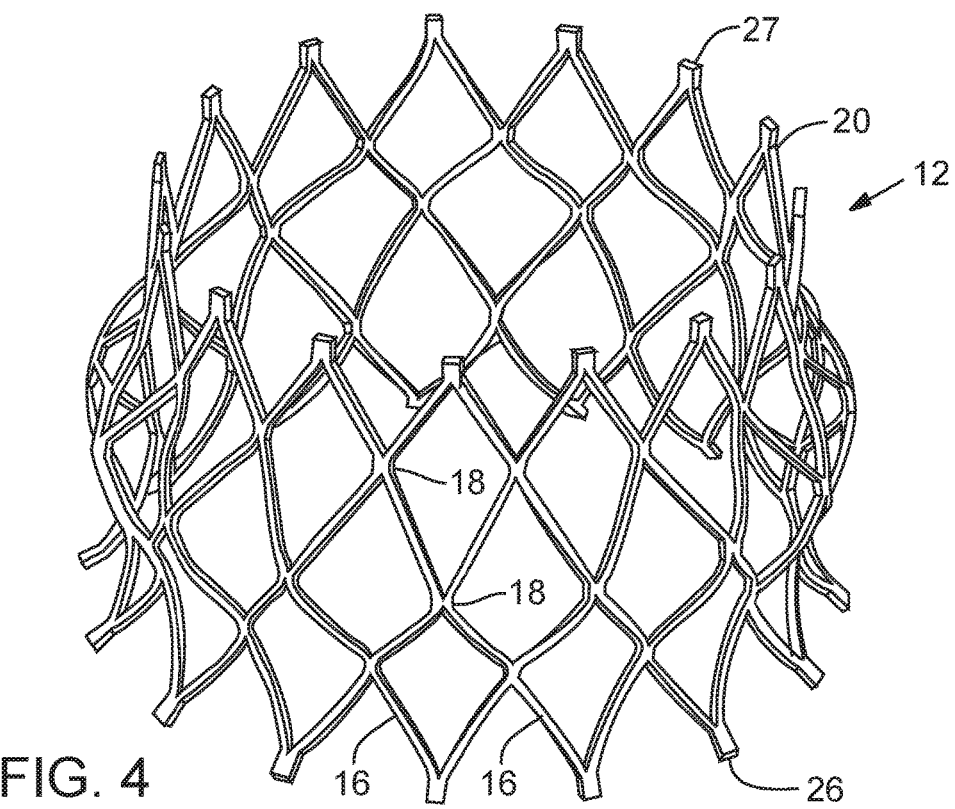
FIG. 4 is a perspective view of the support frame of the prosthetic valve of FIG. 1.

FIGS. 3 and 4 show the stent 12 without the leaflet section 14 for purposes of illustration. As shown, the stent 12 can be formed from a plurality of longitudinally extending, generally sinusoidal shaped frame members, or struts, 16. The struts 16 are formed with alternating bends and are welded or otherwise secured to each other at nodes 18 formed from the vertices of adjacent bends so as to form a mesh structure. The struts 16 can be made of a suitable shape memory material, such as the nickel titanium alloy known as Nitinol, that allows the prosthetic valve to be compressed to a reduced diameter for delivery in a delivery apparatus (such as described below) and then causes the prosthetic valve to expand to its functional size inside the patient's body when deployed from the delivery apparatus. If the prosthetic valve is a balloon-expandable prosthetic valve that is adapted to be crimped onto an inflatable balloon of a delivery apparatus and expanded to its functional size by inflation of the balloon, the stent 12 can be made of a suitable ductile material, such as stainless steel.

The stent 12 has an inflow end 26 and an outflow end 27. The mesh structure formed by the struts 16 comprises a generally cylindrical "upper" or outflow end portion 20, an outwardly bowed or distended intermediate section 22, and an inwardly bowed "lower" or inflow end portion 24. The intermediate section 22 desirably is sized and shaped to extend into the Valsalva sinuses in the root of the aorta to assist in anchoring the prosthetic valve in place once implanted. As shown, the mesh structure desirably has a curved shape along its entire length that gradually increases in diameter from the outflow end portion 20 to the intermediate section 22, then gradually decreases in diameter from the intermediate section 22 to a location on the inflow end portion 24, and then gradually increases in diameter to form a flared portion terminating at the inflow end 26.

Figure 5A:
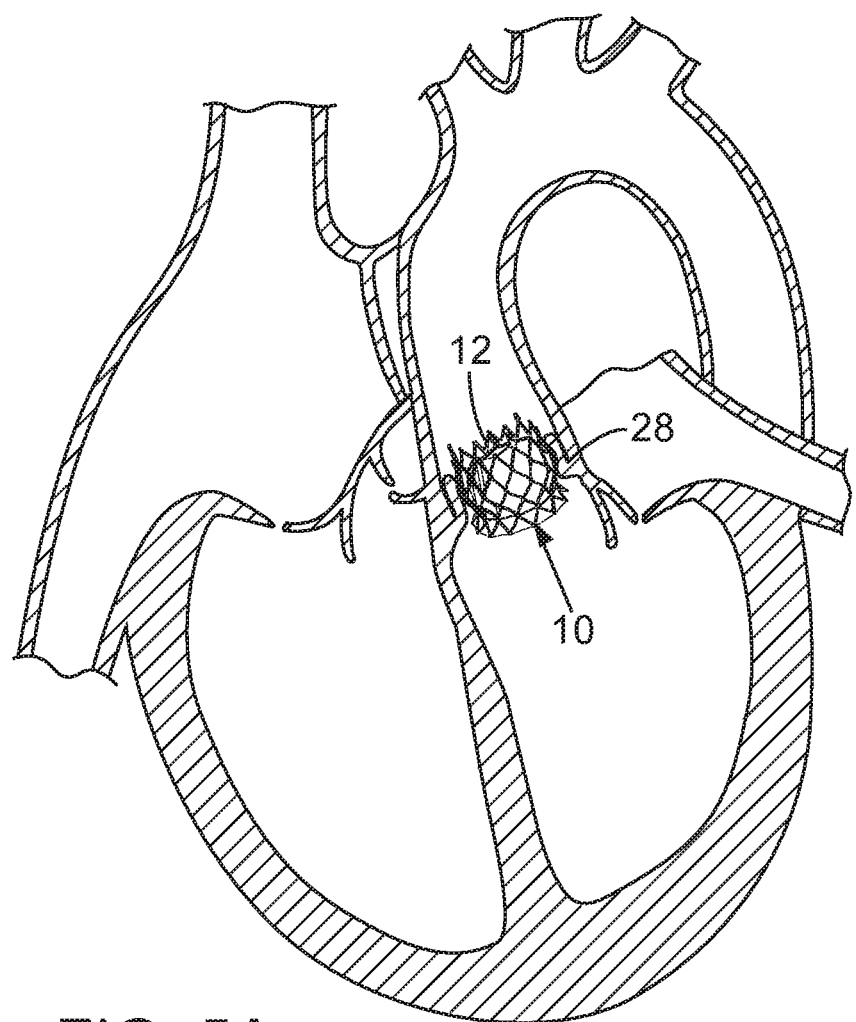
FIG. 5A is a cross-sectional view of the heart showing the prosthetic valve of FIG. 1 implanted within the aortic annulus.
Figure 5B:
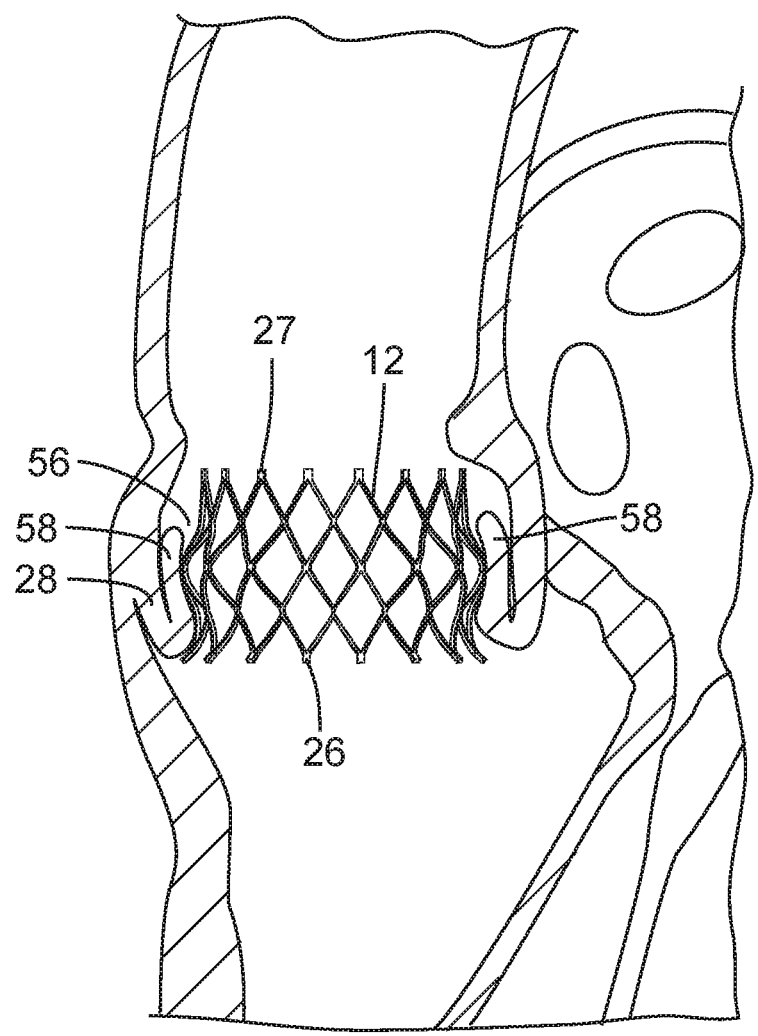
FIG. 5B is an enlarged view of FIG. 5A illustrating the prosthetic valve implanted within the aortic annulus, shown with the leaflet structure of the prosthetic valve removed for clarity.

When the prosthetic valve is in its expanded state, the intermediate section 22 has a diameter $D_1$, the inflow end portion 24 has a minimum diameter $D_2$, the inflow end 26 has a diameter $D_3$, and the outflow end portion 20 has a diameter $D_4$, where $D_2$ is less than $D_1$ and $D_3$, and $D_4$ is less than $D_2$. In addition, $D_1$ and $D_3$ desirably are greater than the diameter of the native annulus in which the prosthetic valve is to be implanted. In this manner, the overall shape of the stent 12 assists in retaining the prosthetic valve at the implantation site. More specifically, and referring to FIGS. 5A and 5B, the prosthetic valve 10 can be implanted within a native valve (the aortic valve in the illustrated example) such that the lower section 24 is positioned within the aortic annulus 28, the intermediate section 24 extends above the aortic annulus into the Valsalva's sinuses 56, and the lower flared end 26 extends below the aortic annulus. The prosthetic valve 10 is retained within the native valve by the radial outward force of the lower section 24 against the surrounding tissue of the aortic annulus 28 as well as the geometry of the stent. Specifically, the intermediate section 24 and the flared lower end 26 extend radially outwardly beyond the aortic annulus 28 to better resist against axial dislodgement of the prosthetic valve in the upstream and downstream directions (toward and away from the aorta). Depending on the condition of the native leaflets 58, the prosthetic valve 10 typically is deployed within the native annulus 28 with the native leaflets 58 folded upwardly and compressed between the outer surface of the stent 12 and the walls of the Valsalva sinuses, as depicted in FIG. 5B. In some cases, it may be desirable to excise the leaflets 58 prior to implanting the prosthetic valve 10.

Known prosthetic valves having a self-expanding frame typically have additional anchoring devices or frame portions that extend into and become fixed to non-diseased areas of the vasculature. Because the shape of the stent 12 assists in retaining the prosthetic valve, additional anchoring devices are not required and the overall length L of the stent can be minimized to prevent the stent upper portion 20 from extending into the non-diseased area of the aorta, or to at least minimize the extent to which the upper portion 20 extends into the non-diseased area of the aorta. Avoiding the non-diseased area of the patient's vasculature helps avoid complications if future intervention is required. For example, the prosthetic valve can be more easily removed from the patient because the stent is primarily anchored to the diseased part of the native valve. Furthermore, a shorter prosthetic valve is more easily navigated around the aortic arch.

In particular embodiments, for a prosthetic valve intended for use in a 22-mm to 24-mm annulus, the diameter D1 is about 28 mm to about 32 mm, with 30 mm being a specific example; the diameter D2 is about 24 mm to about 28 mm, with 26 mm being a specific example; the diameter D3 is about 28 mm to about 32 mm, with 30 mm being a specific example; and the diameter D4 is about 24 mm to about 28 mm, with 26 mm being a specific example. The length L in particular embodiments is about 20 mm to about 24 mm, with 22 mm being a specific example.

Referring again to FIG. 1, the stent 12 can have a plurality of angularly spaced retaining arms, or projections, in the form of posts 30 (three in the illustrated embodiment) that extend from the stent upper portion 20. Each retaining arm 30 has a respective aperture 32 that is sized to receive prongs of a valve-retaining mechanism that can be used to form a releasable connection between the prosthetic valve and a delivery apparatus (described below). In alternative embodiments, the retaining arms 30 need not be provided if a valve-retaining mechanism is not used.

Figure 6:
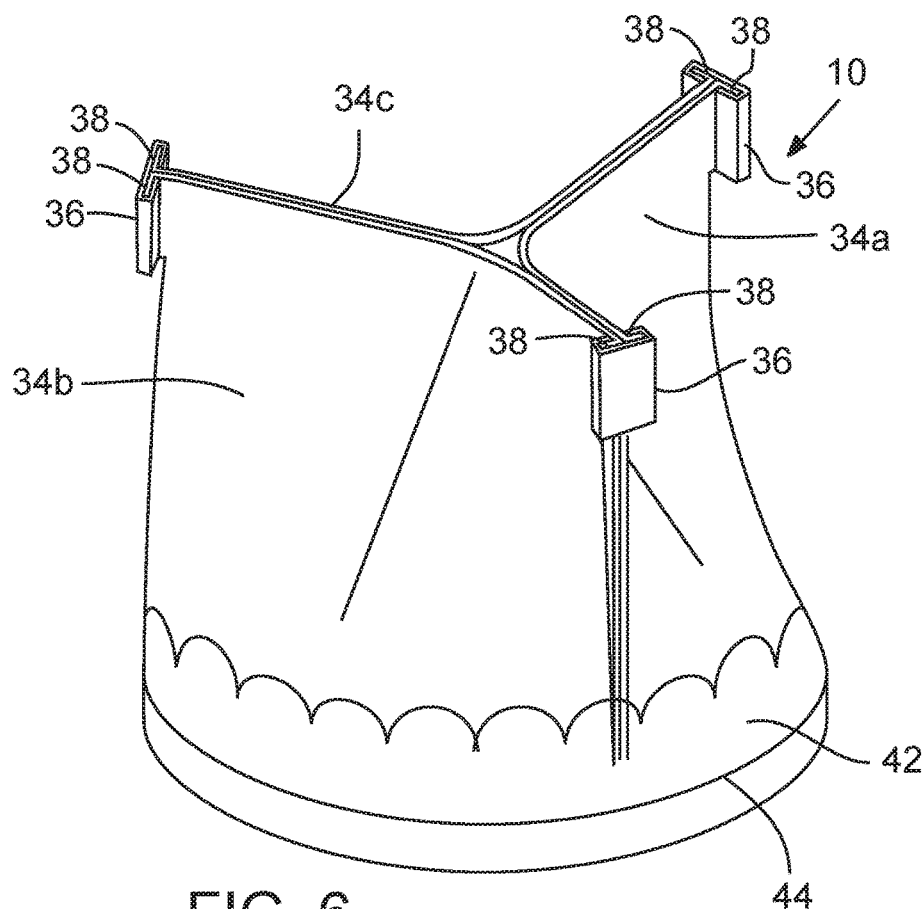
FIG. 6 is a perspective view of the leaflet structure of the prosthetic valve of FIG. 1 shown prior to being secured to the support frame.
Figure 7:
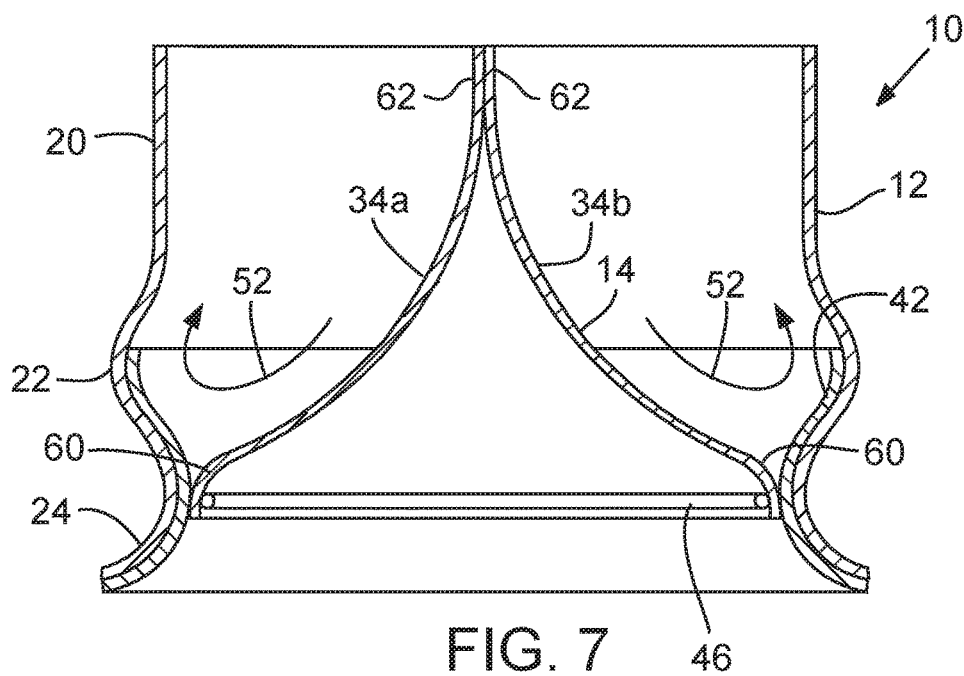
FIG. 7 is a cross-sectional view of the prosthetic valve of FIG. 1.

As best shown in FIGS. 6 and 7, the leaflet assembly 14 in the illustrated embodiment comprises three leaflets 34a, 34b, 34c made of a flexible material. Each leaflet has an inflow end portion 60 and an outflow end portion 62. The leaflets can comprise any suitable biological material (e.g., pericardial tissue, such as bovine or equine pericadium), bio-compatible synthetic materials, or other such materials, such as those described in U.S. Pat. No. 6,730,118, which is incorporated herein by reference. The leaflet assembly 14 can include an annular reinforcing skirt 42 that is secured to the outer surfaces of the inflow end portions of the leaflets 34a, 34b, 34c at a suture line 44 adjacent the inflow end of the prosthetic valve. The inflow end portion of the leaflet assembly 14 can be secured to the stent 12 by suturing the skirt 42 to struts 16 of the lower section 24 of the stent (best shown in FIG. 1). As shown in FIG. 7, the leaflet assembly 14 can further include an inner reinforcing strip 46 that is secured to the inner surfaces of the inflow end portions 60 of the leaflets.

Figure 2:
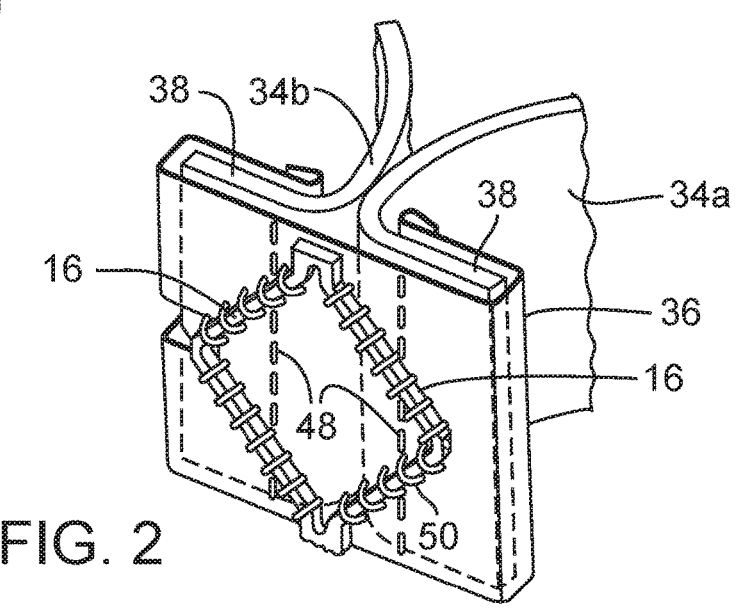
FIG. 2 is a perspective view of a portion of the prosthetic valve of FIG. 1 illustrating the connection of two leaflets to the support frame of the prosthetic valve.

Referring to FIGS. 1 and 2, the outflow end portion of the leaflet assembly 14 can be secured to the upper portion of the stent 12 at three angularly spaced commissure attachments of the leaflets 34a, 34b, 34c. As best shown in FIG. 2, each commissure attachment can be formed by wrapping a reinforcing section 36 around adjacent upper edge portions 38 of a pair of leaflets at the commissure formed by the two leaflets and securing the reinforcing section 36 to the edge portions 38 with sutures 48. The sandwiched layers of the reinforcing material and leaflets can then be secured to the struts 16 of the stent 12 with sutures 50 adjacent the outflow end of the stent. The leaflets therefore desirably extend the entire length or substantially the entire length of the stent from the inflow end 26 to the outflow end 27. The reinforcing sections 36 reinforce the attachment of the leaflets to the stent so as to minimize stress concentrations at the suture lines and avoid "needle holes" on the portions of the leaflets that flex during use. The reinforcing sections 36, the skirt 42, and the inner reinforcing strip 46 desirably are made of a bio-compatible synthetic material, such as polytetrafluoroethylene (PTFE), or a woven fabric material, such as woven polyester (e.g., polyethylene terephtalate (PET)).

FIG. 7 shows the operation of the prosthetic valve 10. During diastole, the leaflets 34a, 34b, 34c collapse to effectively close the prosthetic valve. As shown, the curved shape of the intermediate section 22 of the stent 12 defines a space between the intermediate section and the leaflets that mimics the Valsalva sinuses. Thus, when the leaflets close, backflow entering the "sinuses" creates a turbulent flow of blood along the upper surfaces of the leaflets, as indicated by arrows 52. This turbulence assists in washing the leaflets and the skirt 42 to minimize clot formation.

The prosthetic valve 10 can be implanted in a retrograde approach where the prosthetic valve, mounted in a crimped state at the distal end of a delivery apparatus, is introduced into the body via the femoral artery and advanced through the aortic arch to the heart, as further described in U.S. Patent Publication No. 2008/0065011, which is incorporated herein by reference.

FIGS. 8 and 9 show a delivery apparatus 100, according to one embodiment, that can be used to deliver a self-expanding prosthetic valve, such as prosthetic valve 10 described above, through a patient's vasculature. The delivery apparatus 100 comprises a first, outermost or main catheter 102 (shown alone in FIG. 10) having an elongated shaft 104, the distal end of which is coupled to a delivery sheath 106 (FIG. 18; also referred to as a delivery cylinder). The proximal end of the main catheter 102 is connected to a handle of the delivery apparatus.

FIGS. 23-26 show an embodiment of a handle mechanism having an electric motor for operating the delivery apparatus. The handle mechanism is described in detail below. During delivery of a prosthetic valve, the handle can be used by a surgeon to advance and retract the delivery apparatus through the patient's vasculature. Although not required, the main catheter 102 can comprise a guide catheter that is configured to allow a surgeon to guide or control the amount of bending or flexing of a distal portion of the shaft 104 as it is advanced through the patient's vasculature, such as further described below. Another embodiment of a guide catheter is disclosed in U.S. Patent Publication No. 2008/0065011, which is incorporated herein by reference.

As best shown in FIG. 9, the delivery apparatus 100 also includes a second, intermediate catheter 108 (also referred to herein as a torque shaft catheter) having an elongated shaft 110 (also referred to herein as a torque shaft) and an elongated screw 112 connected to the distal end of the shaft 110. The shaft 110 of the intermediate catheter 108 extends coaxially through the shaft 104 of the main catheter 102. The delivery apparatus 100 can also include a third, nose-cone catheter 118 having an elongated shaft 120 and a nose piece, or nose cone, 122 secured to the distal end portion of the shaft 120. The nose piece 122 can have a tapered outer surface as shown for atraumatic tracking through the patient's vasculature.

The shaft 120 of the nose-cone catheter 118 extends through the prosthetic valve 10 (not shown in FIGS. 8-9) and the shaft 110 of the intermediate catheter 108. In the illustrated configuration, the innermost shaft 120 is configured to be moveable axially and rotatably relative to the shafts 104, 110, and the torque shaft 110 is configured to be rotatable relative to the shafts 104, 120 to effect valve deployment and release of the prosthetic valve from the delivery apparatus, as described in detail below. Additionally, the innermost shaft 120 can have a lumen for receiving a guide wire so that the delivery apparatus can be advanced over the guide wire inside the patient's vasculature.

As best shown in FIG. 10, the outer catheter 102 can comprise a flex control mechanism 168 at a proximal end thereof to control the amount the bending or flexing of a distal portion of the outer shaft 104 as it is advanced through the patient's vasculature, such as further described below. The outer shaft 104 can comprise a proximal segment 166 that extends from the flex control mechanism 168 and a distal segment 126 that comprises a slotted metal tube that increases the flexibility of the outer shaft at this location. The distal end portion of the distal segment 126 can comprises an outer fork 130 of a valve-retaining mechanism 114 (FIG. 8) that is configured to releasably secure a prosthetic valve 10 to the delivery apparatus 100 during valve delivery, as described in detail below.

Figure 28A:
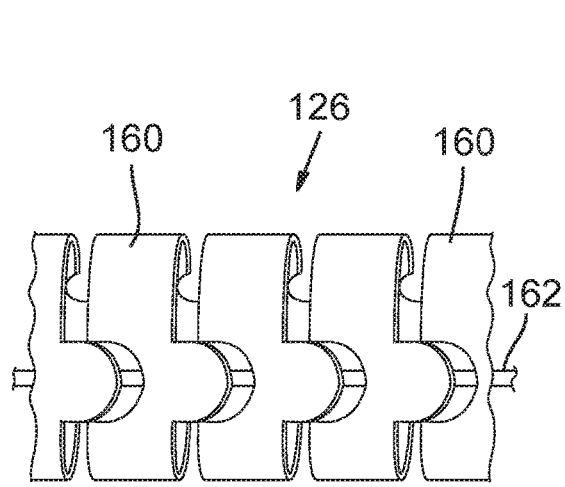
FIG. 28A is an enlarged view of a distal segment of the guide catheter shaft of FIG. 10.
Figure 28B:
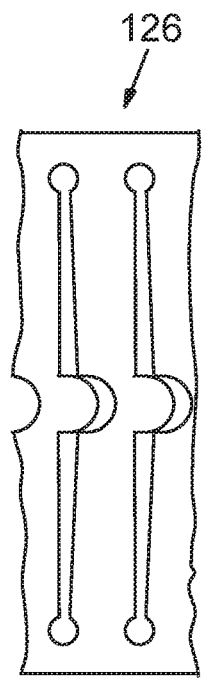
FIG. 28B shows the cut pattern for forming the portion of the shaft shown in FIG. 28A, such as by laser cutting a metal tube.

FIG. 28A is an enlarged view of a portion of the distal segment 126 of the outer shaft 104. FIG. 28B shows the cut pattern that can be used to form the distal segment 126 by laser cutting the pattern in a metal tube. The distal segment 126 comprises a plurality of interconnected circular bands or links 160 forming a slotted metal tube. A pull wire 162 can be positioned inside the distal segment 126 and can extend from a location 164 of the distal segment 126 (FIGS. 10 and 12) to the flex control mechanism. The distal end of the pull wire 162 can be secured to the inner surface of the distal segment 126 at location 164, such as by welding. The proximal end of the pull wire 162 can be operatively connected to the flex control mechanism 168, which is configured to apply and release tension to the pull wire in order to control bending of the shaft, as further described below. The links 160 of the shaft and the gaps between adjacent links are shaped to allow bending of the shaft upon application of light pulling force on the pull wire 162. In the illustrated embodiment, as best shown in FIG. 12, the distal segment 126 is secured to a proximal segment 166 having a different construction (e.g., one or more layers of polymeric tubing). In the illustrated embodiment, the proximal segment 166 extends from the flex control mechanism 168 to the distal segment 126 and therefore makes up the majority of the length of the outer shaft 104. In alternative embodiments, the entire length or substantially the entire length of the outer shaft 104 can be formed from a slotted metal tube comprising one or more sections of interconnected links 160. In any case, the use of a main shaft having such a construction can allow the delivery apparatus to be highly steerable, especially when use in combination with a torque shaft having the construction shown in FIGS. 13 and 14 (described below).

The width of the links 160 can be varied to vary the flexibility of the distal segment along its length. For example, the links within the distal end portion of the slotted tube can be relatively narrower to increase the flexibility of the shaft at that location while the links within the proximal end portion of the slotted tube can be relatively wider so that the shaft is relatively less flexible at that location.

Figure 29A:
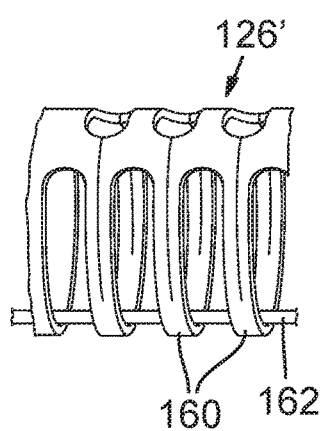
FIG. 29A is an enlarged view of a distal segment of a guide catheter shaft, according to another embodiment.
Figure 29B:
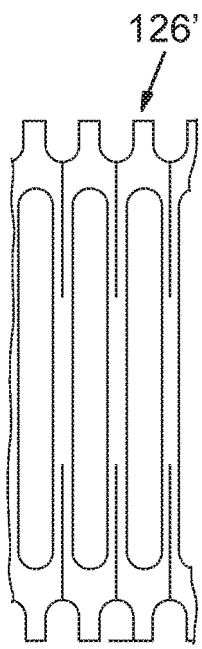
FIG. 29B shows the cut pattern for forming the shaft of FIG. 29A, such as by laser cutting a metal tube.

FIG. 29A shows an alternative embodiment of a distal segment, indicated at 126', which can be formed, for example, by laser cutting a metal tube. The segment 126' can comprise the distal segment of an outer shaft of a delivery apparatus (as shown in FIG. 12) or substantially the entire length of an outer shaft can have the construction shown in FIG. 29A. FIG. 29B shows the cut pattern for forming the segment 126'. In another embodiment, a delivery apparatus can include a composite outer shaft comprising a laser-cut metal tube laminated with a polymeric outer layer that is fused within the gaps in the metal layer. In one example, a composite shaft can comprise a laser cut metal tube having the cut pattern of FIGS. 29A and 29B and a polymeric outer layer fused in the gaps between the links 160 of the metal tube. In another example, a composite shaft can comprise a laser cut metal tube having the cut pattern of FIGS. 28A and 28B and a polymeric outer layer fused in the gaps between the links 160 of the metal tube. A composite shaft also can include a polymeric inner layer fused in the gaps between the links 160 of the metal tube.

Referring to FIGS. 8A and 11, the flex control mechanism 168 can comprise a rotatable housing, or handle portion, 186 that houses a slide nut 188 mounted on a rail 190. The slide nut 188 is prevented from rotating within the housing by one or more rods 192, each of which is partially disposed in a corresponding recess within the rail 190 and a slot or recess on the inside of the nut 188. The proximal end of the pull wire 162 is secured to the nut 188. The nut 188 has external threads that engage internal threads of the housing 186. Thus, rotating the housing 186 causes the nut 188 to move axially within the housing in the proximal or distal direction, depending on the direction of rotation of the housing. Rotating the housing in a first direction (e.g., clockwise), causes the nut 188 to travel in the proximal direction, which applies tension to the pull wire 162, which causes the distal end of the delivery apparatus to bend or flex. Rotating the housing 186 in a second direction (e.g., counterclockwise), causes the nut 188 to travel in the distal direction, which relieves tension in the pull wire 162 and allows the distal end of the delivery apparatus to flex back to its pre-flexed configuration under its own resiliency.

FIGS. 30A-30C illustrate an alternative implementation of a flex control mechanism 300, which includes a clutch mechanism that permits a travelling component, such as the slide nut 188, to engage and disengage from the threads of an elongated component, such as a handle portion, or housing, 304. With reference to FIG. 30A, the housing 304 includes an engagement portion 308 located along a proximal end portion 310 of the housing 304. The engagement portion 308 includes threads or grooves 314 for engaging the threads or grooves 316 of the slide nut 188 (as best shown in FIG. 30C). The housing 304 further includes a disengagement portion 320 located along the distal end portion 322 of the housing 304. The disengagement portion 320 lacks the threads or grooves of the engagement portion 308, such as having a smooth annular surface. In other implementations, the disengagement portion 320 may have a different configuration, provided that the slide nut 188 does not move axially with respect to the housing 304 by further rotation of the housing 304 when all of the threads 316 of the nut 188 disengage from the threads 314 of the engagement portion 308 and are received in the disengagement portion 320.

The rail 190 desirably extends the entire, or substantially the entire, combined length of the engagement portion 308 and the disengagement portion 320, such that the nut 188 is supported on the rail 190 as the nut 188 is moved axially between the engagement portion 308 and the disengagement portion 320, as further described below. One or more rods 192 (not shown in FIG. 30A-30C, but analogous to the rods 192 of FIG. 11) also desirably extend the entire, or substantially the entire, combined length of the engagement portion 308 and the disengagement portion 320, so that the nut 188 remains engaged with the one or more rods 192 as the nut 188 is moved axially between the engagement portion 308 and the disengagement portion 320.

In at least certain implementations, the size of the disengagement portion 320 is at least about as large, such as being as large or larger than, the threaded portion of the slide nut 188. For example, the disengagement portion 320 may have a diameter and length greater than at least the threaded portion of the slide nut 188, or otherwise be sized to receive all, or at least the threaded portion, of the slide nut 188. The disengagement portion 320 may have a different size, in other examples, provided that the slide nut 188 does not move axially with respect to the housing 304 by further rotation of the housing 304 when all of the threads 316 of the slide nut 188 disengage from the threads 314 of the engagement portion 308 and are received within the disengagement portion 320.

Thus, when the slide nut 188 is positioned in the engagement portion 308, rotation of the housing 304 causes the slide nut 188 to move axially to adjust the tension in a pull wire (not shown in FIGS. 30A-30C, but analogous to the pull wire 162 of FIG. 11, as described above). When the housing 304 is rotated to move the slide nut 188 distally in the direction of arrow 324, the threads 316 of the slide nut 188 eventually disengage from threads 314 of the housing 304. When all of the threads 316 of the slide nut 188 disengage from the threads 314 of the housing 304 and are received in the disengagement portion 320 (FIG. 30C), further rotation of the housing 304 does not cause the slide nut 188 to move axially in the distal direction.

In this manner, the flex control mechanism 300 can allow a user to rotate the housing 304 without causing the slide nut 188 to abut and exert undue pressure against the distal end of the housing 304, or components thereof, such as a ring or bushing 328 disposed at the distal end of the housing 304, as may happen if the threads or grooves 314 of the housing 304 extended further towards the distal end 322 of the housing 304.

In particular examples, the housing 304 includes a biasing device 332 configured to promote re-engagement of the threads 316 of the slide nut 188 with the threads 314 of the housing 304. In this manner, the biasing device 332 and the disengagement portion 320 of the housing 304 function as a clutch mechanism that engages and disengages the slide nut 188 from the threads 314 of the housing 304. The biasing device 332 may be, for example, a spring, a spring washer (such as a Belleville washer), or a resilient material, including an elastomer, such as rubber, or a foam. As shown in FIG. 30A, the biasing device 332 in the illustrated embodiment can be located within the disengagement portion 320 and has one end that abuts the ring 328 and an opposite end that abuts the slide nut 188. The biasing device 332 is configured to exert an axial, proximally directed force against the slide nut 188 when the slide nut 188 is moved into contact with the biasing device 332. For example, the biasing device 332 may be selected such that it exerts a desired amount of force against the slide nut 188. When the biasing device 332 is a spring, the spring may be selected to have a sufficiently large spring constant to exert the desired amount of axial force.

The biasing device 332 may be selected based on additional properties, in further examples. The biasing device 332 may be selected, for example, to provide tactile or audible feedback to a user when the biasing device 332 reaches a particular level of compression, such as being fully compressed. The tactile or audible feedback may be provided, for example, by selecting a spring with an appropriate spring constant.

FIG. 30B illustrates the slide nut 188 having been moved into contact with the biasing device 332. As shown in FIG. 30C, continued rotation of the housing 304 causes the slide nut 188 to enter the disengagement portion 320 and to compress the biasing device 332. The biasing device 332 exerts an axial, proximally-directed force against the slide nut 188. As discussed above, when the entire threaded portion of the slide nut 188 is received with the disengagement portion 320, further rotation of the housing 304 does not cause distal axial movement of the slide nut 188. However, if the direction of rotational movement of the housing 304 is reversed, the biasing device 332 will urge the threads 316 of the slide nut 188 into reengagement with the threads 314 of the housing 304, and cause the slide nut 188 to move proximally along the engagement section 308.

Although FIGS. 30A-30C illustrate a disengagement portion 320 and biasing device 332 at the distal end 322 of the housing 304, it should be appreciated that the flex control mechanism 300 may have other configurations. For example, the housing 304 may include a disengagement portion, and optionally a biasing device, at the proximal end 310 of the housing 304, in place of, or in addition to, the disengagement portion 320 and biasing device 332 located at the distal end 322 of the housing 304.

Figure 13:
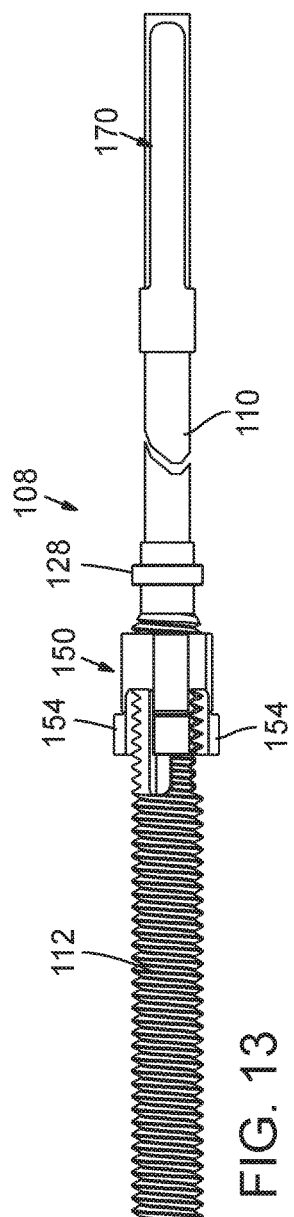
FIG. 13 is a side view of the torque shaft catheter of the delivery apparatus of FIG. 8.
Figure 14:
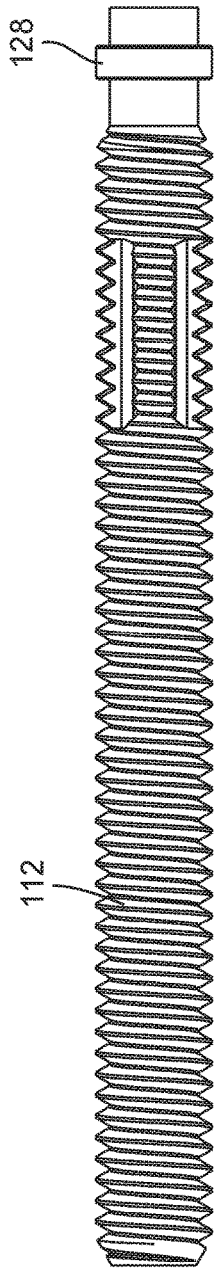
FIG. 14 is an enlarged side view of the rotatable screw of the torque shaft catheter of FIG. 13.

As best shown in FIG. 13, the torque shaft catheter 108 includes an annular projection in the form of a ring 128 (also referred to as an anchoring disc) mounted on the distal end portion of the torque shaft 110 adjacent the screw 112. The ring 128 is secured to the outer surface of the torque shaft 110 such that it cannot move axially or rotationally relative to the torque shaft. The inner surface of the outer shaft 104 is formed with a feature, such as a slot or recess, that receives the ring 128 in such a manner that the ring and the corresponding feature on the inner surface of the outer shaft 104 allow the torque shaft 110 to rotate relative to the outer shaft 104, but prevent the torque shaft from moving axially relative to the outer shaft. The corresponding feature on the outer shaft 104 that receives the ring 128 can be inwardly extending tab portions formed in the distal segment 126, such as shown at 164 in FIG. 12. In the illustrated embodiment (as best shown in FIG. 14), the ring 128 is an integral part of the screw 112 (i.e., the screw 112 and the ring 128 are portions of single component). Alternatively, the screw 112 and the ring 128 are separately formed components but are both fixedly secured to the distal end of the torque shaft 110.

Figure 16:
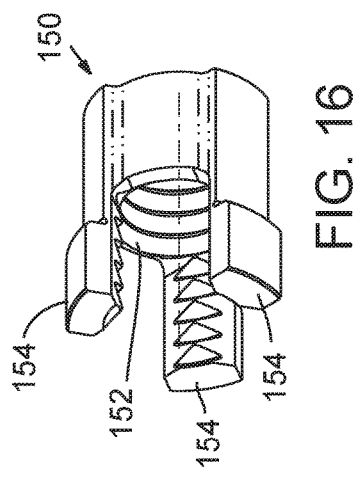
FIG. 16 is an enlarged perspective view of the threaded nut used in the torque shaft catheter of FIG. 13.

The torque shaft 110 desirably is configured to be rotatable relative to the delivery sheath 106 to effect incremental and controlled advancement of the prosthetic valve 10 from the delivery sheath 106. To such ends, and according to one embodiment, the delivery apparatus 100 can include a sheath retaining ring in the form of a threaded nut 150 mounted on the external threads of the screw 112. As best shown in FIG. 16, the nut 150 includes internal threads 152 that engage the external threads of the screw 112 and axially extending legs 154. Each leg 154 has a raised distal end portion that extends into and/or forms a snap fit connection with openings 172 in the proximal end of the sheath 106 (as best shown in FIG. 18) so as to secure the sheath 106 to the nut 150. As illustrated in FIGS. 17B and 18, the sheath 106 extends over the prosthetic valve 10 and retains the prosthetic valve in a radially compressed state until the sheath 106 is retracted by the user to deploy the prosthetic valve.

Figure 21:
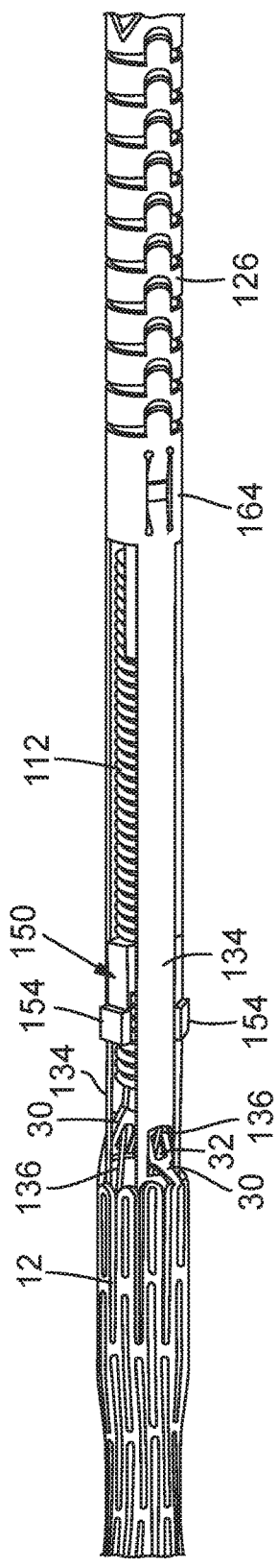
FIGS. 21 and 22 are enlarged side views of a distal end portion of the delivery apparatus of FIG. 8, illustrating the operation of the torque shaft for deploying a prosthetic valve from a delivery sheath.
Figure 22:
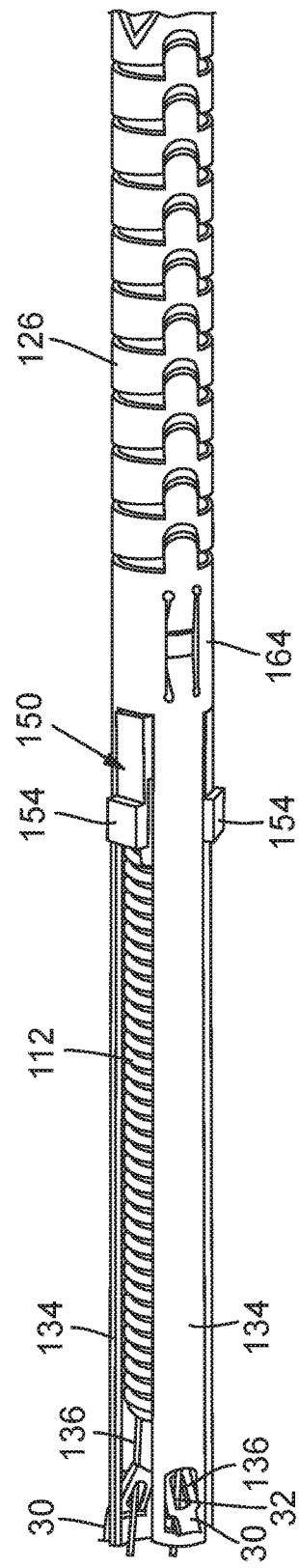

As best shown in FIGS. 21 and 22, the outer fork 130 (FIG. 10) of the valve-retaining mechanism comprises a plurality of prongs 134, each of which extends through a region defined between two adjacent legs 154 of the nut so as to prevent rotation of the nut 150 relative to the screw 112 upon rotation of the screw. As such, rotation of the torque shaft 110 (and thus the screw 112) causes corresponding axial movement of the nut 150. The connection between the nut 150 and the sheath 106 is configured such that axial movement of the nut along the screw 112 (in the distal or proximal direction) causes the sheath 106 to move axially in the same direction relative to the screw and the valve-retaining mechanism.

FIG. 21 shows the nut 150 in a distal position wherein the sheath 106 (not shown in FIG. 21) extends over and retains the prosthetic valve 10 in a compressed state for delivery. Movement of the nut 150 from the distal position (FIG. 21) to a proximal position (FIG. 22) causes the sheath 106 to move in the proximal direction, thereby deploying the prosthetic valve 10 from the sheath 106. Rotation of the torque shaft 110 to effect axial movement of the sheath 106 can be accomplished with a motorized mechanism (such as shown in FIGS. 23-26 and described below) or by manually turning a crank or wheel.

Figure 31A:
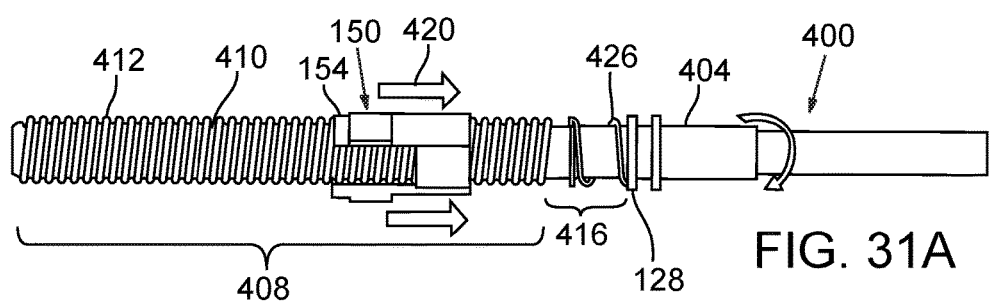
FIG. 31A is a side view of an alternative implementation of a torque shaft catheter useable in the delivery apparatus of FIG. 8.
Figure 31B:
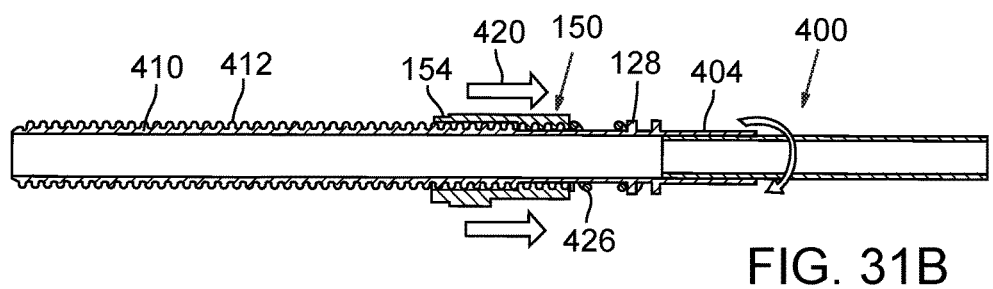
FIGS. 31B and 31C are cross-sectional views of the torque shaft catheter of FIG. 31A.
Figure 31C:
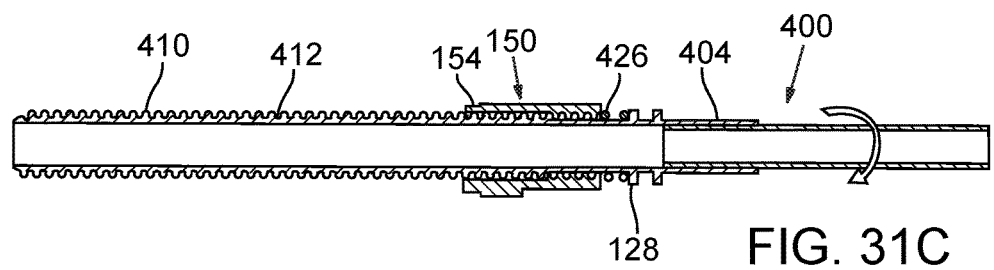

FIGS. 31A-31C illustrate an alternative implementation 400 of a torque shaft catheter (generally similar to the torque shaft catheter 108 of FIG. 13), which in this implementation includes a clutch mechanism that allows a travelling component, such as the nut 150, to engage and disengage from an elongated component, such as a screw 410.

The torque shaft 404 in this embodiment includes an engagement portion 408 corresponding to a screw 410, and thus includes threads or grooves 412 for engaging the mating threads or grooves 152 on the nut 150 (as best shown in FIG. 16). When the nut 150 is positioned on the screw 410, rotation of the torque shaft 404 causes the nut 150 to move axially along the screw 410, thereby moving the sheath 106, as discussed above.

The torque shaft 404 further includes a disengagement portion 416. The disengagement portion 416 lacks threads or grooves, such as having a smooth annular surface. In further implementations, the disengagement portion 416 has a different configuration, provided that the nut 150 does not move axially with respect to the torque shaft 404 by further rotation of the torque shaft when all of the threads 152 of the nut 150 disengage from the threads 412 of the screw 410.

In at least certain implementations, the size of the disengagement portion 416 is at least about as large, such as being as large or larger than, the threaded portion of the nut 150. For example, the disengagement portion 416 may have a length greater than at least the threaded portion of the nut 150, or otherwise be sized to receive all, or at least the threaded portion, of the nut 150. In the embodiment of FIGS. 31A-31C, the threads 152 are only on a proximal portion of the nut 150 (the portion of the nut between the proximal ends of the legs 154 and the proximal end of the nut) and not on the legs. As such, the disengagement portion 416 has an axial length at least greater than the length of the proximal portion of the nut 150.

In other implementations, the disengagement portion 416 may have a different size and/or shape, provided that the nut 150 does not move axially with respect to the torque shaft 404 by further rotation of the torque shaft 404 when all of the threads 152 of the nut 150 disengage from the threads 412 of the screw 410. For example, if the legs 154 of the nut 150 are threaded, the size of the disengagement portion 416 may be correspondingly increased.

When the torque shaft 404 is rotated to move the nut 150 and the sheath 106 proximally in the direction of arrow 420, the threads 152 of the nut 150 eventually disengage from the threads 412 of the screw 410. When all of the threads 152 of the nut 150 disengage from the threads 412 of the screw 410 (FIG. 31C), further rotation of the torque shaft 404 does not cause the nut 150 to move axially in the proximal direction. In this manner, the torque shaft catheter 400 can allow a user to freely rotate the torque shaft 404 without causing the nut 150 to abut and exert undue pressure against the annular projection 128 once the nut 150 reaches the end of the screw 410, thereby avoiding torque build-up and undesirable stress on the components of the delivery apparatus.

In particular examples, the torque shaft catheter 400 includes a biasing device 426 configured to promote re-engagement of the threads 152 of the nut 150 with the threads 412 of the screw 410. In this manner, the biasing device 426 and the disengagement portion 416 of the torque shaft 404 function as a clutch mechanism that engages and disengages the nut 150 from the screw 410. The biasing device 426 may be, in various implementations, a spring, a spring washer (such as a Belleville washer), or a resilient material, including elastomers, such as rubber, or foam.

As shown in FIG. 31A, the biasing device 426 in the illustrated embodiment is co-axially disposed on the torque shaft 404, within the disengagement portion 416, and has one end that abuts the annular projection 128 and an opposite end that abuts the nut 150. The biasing device 426 is configured to exert an axial, distally directed, force against the nut 150 when the nut is moved into contact with the biasing device. For example, the biasing device 426 may be selected such that it exerts a desired amount of force against the nut 150. When the biasing device 426 is a spring, the spring may be selected to have a sufficiently large spring constant to exert the desired amount of axial force.

The biasing device 426 may be selected based on additional properties, in further examples. The biasing device 426 may be selected, in some examples, to provide tactile or audible feedback to a user when the biasing device 426 reaches a particular level of compression, such as being fully compressed. The tactile or audible feedback may be provided by, for example, selecting a spring with an appropriate spring constant, such that the spring vibrates sufficiently to be felt by a user, or emits a noise audible to a user, when compressed.

FIG. 31B illustrates the nut 150 having been rotated into contact with the biasing device 426. As shown in FIG. 31C, further rotation of the torque shaft 404 causes the nut 150 to enter the disengagement portion 416, and to compress the biasing device 426. The biasing device 426 exerts an axial, distally directed force against the nut 150. As discussed above, when the entire threaded portion of the nut 150 is received within the disengagement portion 416, further rotation of the torque shaft 404 does not cause axial movement of the nut 150. However, if the direction of rotation of the torque shaft 404 is reversed, the biasing device 426 will urge the threads of the nut 150 into reengagement with the threads 412 of the screw 410, and cause the nut 1 to move distally along the screw.

Although FIGS. 31A-31C illustrate a disengagement portion 416 and biasing device 426 adjacent the proximal end of the screw 410, it should be appreciated that the torque shaft catheter 400 may have other configurations. For example, the torque shaft catheter 400 may include a disengagement portion, and optionally a biasing device, adjacent the distal end of the screw 410, in place of, or in addition to, the disengagement portion 416 and biasing device 426 adjacent the proximal end of the screw 410.

FIG. 17 shows an enlarged view of the nose cone 122 secured to the distal end of the innermost shaft 120. The nose cone 122 in the illustrated embodiment includes a proximal end portion 174 that is sized to fit inside the distal end of the sheath 106. An intermediate section 176 of the nose cone is positioned immediately adjacent the end of the sheath 106 in use and is formed with a plurality of longitudinal grooves, or recessed portions, 178. The diameter of the intermediate section 176 at its proximal end 180 desirably is slightly larger than the outer diameter of the sheath 106.

The proximal end 180 can be held in close contact with the distal end of the sheath 106 to protect surrounding tissue from coming into contact with the metal edge of the sheath. The grooves 178 allow the intermediate section 176 to be compressed radially as the delivery apparatus is advanced through an introducer sheath. This allows the nose cone 122 to be slightly oversized relative to the inner diameter of the introducer sheath. FIG. 17B shows a cross-section of the nose cone 122 and the sheath 106 in a delivery position, with the prosthetic valve retained in a compressed delivery state inside the sheath 106 (for purposes of illustration, only the stent 12 of the prosthetic valve is shown). As shown, the proximal end 180 of the intermediate section 176 can abut the distal end of the sheath 106 and a tapered proximal surface 182 of the nose cone can extend within a distal portion of the stent 12.

As noted above, the delivery apparatus 100 can include a valve-retaining mechanism 114 (FIG. 8B) for releasably retaining a stent 12 of a prosthetic valve. The valve-retaining mechanism 114 can include a first valve-securement component in the form of an outer fork 130 (as best shown in FIG. 12) (also referred to as an "outer trident" or "release trident"), and a second valve-securement component in the form of an inner fork 132 (as best shown in FIG. 17) (also referred to as an "inner trident" or "locking trident"). The outer fork 130 cooperates with the inner fork 132 to form a releasable connection with the retaining arms 30 of the stent 12.

The proximal end of the outer fork 130 is connected to the distal segment 126 of the outer shaft 104, and the distal end of the outer fork is releasably connected to the stent 12. In the illustrated embodiment, the outer fork 130 and the distal segment 126 can be integrally formed as a single component (e.g., the outer fork and the distal segment can be laser cut or otherwise machined from a single piece of metal tubing), although these components can be separately formed and subsequently connected to each other. The inner fork 132 can be mounted on the nose catheter shaft 120 (as best shown in FIG. 17). The inner fork 132 connects the stent to the distal end portion of the nose catheter shaft 120. The nose catheter shaft 120 can be moved axially relative to the outer shaft 104 to release the prosthetic valve from the valve-retaining mechanism, as further described below.

As best shown in FIG. 12, the outer fork 130 includes a plurality of angularly-spaced prongs 134 (three in the illustrated embodiment) corresponding to the retaining arms 30 of the stent 12, which prongs extend from the distal end of distal segment 126. The distal end portion of each prong 134 includes a respective opening 140. As best shown in FIG. 17, the inner fork 132 includes a plurality of angularly-spaced prongs 136 (three in the illustrated embodiment) corresponding to the retaining arms 30 of the stent 12, which prongs extend from a base portion 138 at the proximal end of the inner fork. The base portion 138 of the inner fork is fixedly secured to the nose catheter shaft 120 (e.g., with a suitable adhesive) to prevent axial and rotational movement of the inner fork relative to the nose catheter shaft 120.

Each prong 134 of the outer fork 130 cooperates with a corresponding prong 136 of the inner fork 132 to form a releasable connection with a retaining arm 30 of the stent 12. In the illustrated embodiment, for example, the distal end portion of each prong 134 is formed with an opening 140. When the prosthetic valve 10 is secured to the delivery apparatus (as best shown in FIG. 19), each retaining arm 30 of the stent 12 extends inwardly through an opening 140 of a prong 134 of the outer fork 130 and a prong 136 of the inner fork 132 is inserted through the opening 32 of the retaining arm 30 so as to retain the retaining arm from backing out of the opening 140.

FIG. 19 shows the prosthetic valve 10 secured to the delivery apparatus by the inner 132 and outer 130 forks before the prosthetic valve is loaded into the sheath 106. Retracting the inner prongs 136 proximally (in the direction of arrow 184 in FIG. 20) to remove the inner prongs from the openings 32 is effective to release the prosthetic valve 10 from the retaining mechanism. When the inner fork 132 is moved to a proximal position (FIG. 20), the retaining arms 30 of the stent 12 can move radially outwardly from the openings 140 in the outer fork 130 under the resiliency of the stent. In this manner, the valve-retaining mechanism 114 forms a releasable connection with the prosthetic valve that is secure enough to retain the prosthetic valve relative to the delivery apparatus to allow the user to fine tune or adjust the position of the prosthetic valve after it is deployed from the delivery sheath. When the prosthetic valve is positioned at the desired implantation site, the connection between the prosthetic valve and the retaining mechanism can be released by retracting the nose catheter shaft 120 relative to the outer shaft 104 (which retracts the inner fork 132 relative to the outer fork 130).

Techniques for compressing and loading the prosthetic valve 10 into the sheath 106 are described below. Once the prosthetic valve 10 is loaded in the delivery sheath 106, the delivery apparatus 100 can be inserted into the patient's body for delivery of the prosthetic valve. In one approach, the prosthetic valve can be delivered in a retrograde procedure where a delivery apparatus is inserted into a femoral artery and advanced through the patient's vasculature to the heart. Prior to insertion of the delivery apparatus, an introducer sheath can be inserted into the femoral artery followed by a guide wire, which is advanced through the patient's vasculature through the aorta and into the left ventricle. The delivery apparatus 100 can then be inserted through the introducer sheath and advanced over the guide wire until the distal end portion of the delivery apparatus containing the prosthetic valve 10 is advanced to a location adjacent to or within the native aortic valve.

Thereafter, the prosthetic valve 10 can be deployed from the delivery apparatus 100 by rotating the torque shaft 110 relative to the outer shaft 104. As described below, the proximal end of the torque shaft 110 can be operatively connected to a manually rotatable handle portion or a motorized mechanism that allows the surgeon to effect rotation of the torque shaft 110 relative to the outer shaft 104. Rotation of the torque shaft 110 and the screw 112 causes the nut 150 and the sheath 106 to move in the proximal direction toward the outer shaft (FIG. 22), which deploys the prosthetic valve from the sheath.

Rotation of the torque shaft 110 causes the sheath 106 to move relative to the prosthetic valve in a precise and controlled manner as the prosthetic valve advances from the open distal end of the delivery sheath and begins to expand. Hence, unlike known delivery apparatuses, as the prosthetic valve 10 begins to advance from the delivery sheath 106 and expand, the prosthetic valve is held against uncontrolled movement from the sheath caused by the expansion force of the prosthetic valve against the distal end of the sheath. In addition, as the sheath 106 is retracted, the prosthetic valve 10 is retained in a stationary position relative to the ends of the inner shaft 120 and the outer shaft 104 by virtue of the valve-retaining mechanism 114. As such, the prosthetic valve 10 can be held stationary relative to the target location in the body as the sheath 106 is retracted. Moreover, after the prosthetic valve 10 is partially advanced from the sheath 106, it may be desirable to retract the prosthetic valve back into the sheath, for example, to reposition the prosthetic valve or to withdraw the prosthetic valve entirely from the body. The partially deployed prosthetic valve 10 can be retracted back into the sheath 106 by reversing the rotation of the torque shaft, which causes the sheath to advance back over the prosthetic valve in the distal direction.

In known delivery devices, the surgeon must apply push-pull forces to the shaft and/or the sheath to unsheathe the prosthetic valve. It is therefore difficult to transmit forces to the distal end of the device without distorting the shaft (e.g., compressing or stretching the shaft axially), which in turn causes uncontrolled movement of the prosthetic valve during the unsheathing process. To mitigate this effect, the shaft and/or sheath can be made more rigid, which is undesirable because the device becomes harder to steer through the vasculature. In contrast, the manner of unsheathing the prosthetic valve described above eliminates the application of push-pull forces on the shaft, as required in known devices, so that relatively high and accurate forces can be applied to the distal end of the shaft without compromising the flexibility of the device. In certain embodiments, as much as 20 lbs. of force can be transmitted to the end of the torque shaft without adversely affecting the unsheathing process. In contrast, prior art devices utilizing push-pull mechanisms typically cannot exceed about 5 lbs. of force during the unsheathing process.

After the prosthetic valve 10 is advanced from the delivery sheath 106 and expands to its functional size, the prosthetic valve remains connected to the delivery apparatus via the retaining mechanism 114. Consequently, after the prosthetic valve 10 is advanced from the delivery sheath 106, the surgeon can reposition the prosthetic valve relative to the desired implantation position in the native valve, such as by moving the delivery apparatus in the proximal and distal directions or side to side, or rotating the delivery apparatus, which causes corresponding movement of the prosthetic valve. The retaining mechanism 114 desirably provides a connection between the prosthetic valve 10 and the delivery apparatus that is secure and rigid enough to retain the position of the prosthetic valve relative to the delivery apparatus against the flow of the blood as the position of the prosthetic valve is adjusted relative to the desired implantation position in the native valve.

Once the surgeon positions the prosthetic valve 10 at the desired implantation position in the native valve, the connection between the prosthetic valve and the delivery apparatus can be released by retracting the innermost shaft 120 in the proximal direction relative to the outer shaft 104, which is effective to retract the inner fork 132 to withdraw its prongs 136 from the openings 32 in the retaining arms 30 of the prosthetic valve (FIG. 20). Slightly retracting of the outer shaft 104 allows the outer fork 130 to back off the retaining arms 30 of the prosthetic valve 10, which slide outwardly through openings 140 in the outer fork to completely disconnect the prosthetic valve from the retaining mechanism 114. Thereafter, the delivery apparatus can be withdrawn from the body, leaving the prosthetic aortic valve 10 implanted within the native valve (such as shown in FIGS. 5A and 5B).

The delivery apparatus 100 has at its distal end a semi-rigid segment comprised of relatively rigid components used to transform rotation of the torque shaft into axial movement of the sheath. In particular, this semi-rigid segment in the illustrated embodiment is comprised of the prosthetic valve and the screw 112. An advantage of the delivery apparatus 100 is that the overall length of the semi-rigid segment is minimized because the nut 150 is used rather than internal threads on the outer shaft to affect translation of the sheath 106. The reduced length of the semi-rigid segment increases the overall flexibility along the distal end portion of the delivery catheter. Moreover, the length and location of the semi-rigid segment remains constant because the torque shaft does not translate axially relative to the outer shaft. As such, the curved shape of the delivery catheter can be maintained during valve deployment, which improves the stability of the deployment. A further benefit of the delivery apparatus 100 is that the ring 128 prevents the transfer of axial loads (compression and tension) to the section of the torque shaft 110 that is distal to the ring.

In an alternative embodiment, the delivery apparatus can be adapted to deliver a balloon-expandable prosthetic valve 10. As described above, the valve retaining mechanism 114 can be used to secure the prosthetic valve to the end of the delivery apparatus. Since the stent 12 of the prosthetic valve 10 is not self-expanding, the sheath 106 can be optional. The retaining mechanism 114 enhances the pushability of the delivery apparatus and prosthetic valve assembly through an introducer sheath.

FIGS. 23-26 illustrate the proximal end portion of the delivery apparatus 100, according to one embodiment. The delivery apparatus 100 can comprise a handle 202 that is configured to be releasably connectable to the proximal end portion of a catheter assembly 204 comprising catheters 102, 108, 118. It may be desirable to disconnect the handle 202 from the catheter assembly 204 for various reasons. For example, disconnecting the handle 202 can allow another device to be slid over the catheter assembly 204, such as a valve-retrieval device or a device to assist in steering the catheter assembly. It should be noted that any of the features of the handle 202 and the catheter assembly 204 can be implemented in any of the embodiments of the delivery apparatuses disclosed herein.

FIGS. 23 and 24 show the proximal end portion of the catheter assembly 204 partially inserted into a distal opening of the handle 202. The proximal end portion of the main shaft 104 is formed with an annular groove 212 (as best shown in FIG. 24) that cooperates with a holding mechanism, or latch mechanism, 214 inside the handle 202. When the proximal end portion of the catheter assembly 204 is fully inserted into the handle 202, as shown in FIGS. 25 and 26, an engaging portion 216 of the holding mechanism 214 extends at least partially into the groove 212.

One side of the holding mechanism 214 is connected to a button 218 that extends through the housing of the handle 202. The opposite side of the holding mechanism 214 is contacted by a spring 220 that biases the holding mechanism to a position engaging the main shaft 104 at the groove 212. The engagement of the holding mechanism 214 within the groove 212 prevents axial separation of the catheter assembly 204 from the handle 202. The catheter assembly 204 can be released from the handle 202 by depressing button 218, which moves the holding mechanism 214 from locking engagement with the main shaft 104. Furthermore, the main shaft 104 can be formed with a flat surface portion within the groove 212. The flat surface portion is positioned against a corresponding flat surface portion of the engaging portion 216. This engagement holds the main shaft 104 stationary relative to the torque shaft 110 as the torque shaft is rotated during valve deployment.

Figure 15:
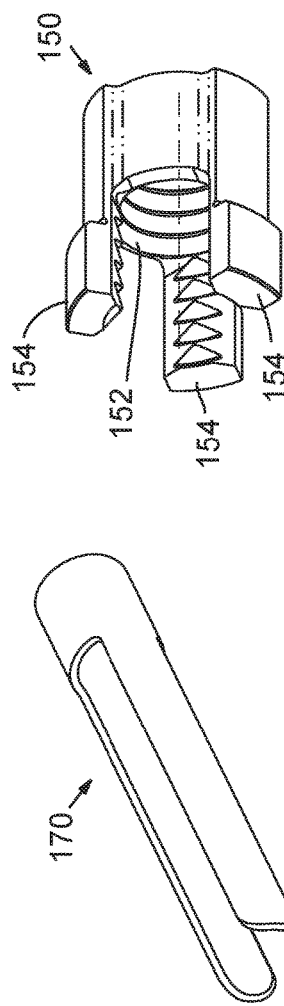
FIG. 15 is an enlarged perspective view of a coupling member that may be disposed at the end of the torque shaft of FIG. 13.

The proximal end portion of the torque shaft 110 can have a driven nut 222 (FIG. 26) that is slidably received in a drive cylinder 224 (FIG. 25) mounted inside the handle 202. The nut 222 can be secured to the proximal end of the torque shaft 100 by securing the driven nut over a coupling member 170 (FIG. 15). FIG. 26 is a perspective view of the inside of the handle 202 with the drive cylinder 224 and other components removed to show the driven nut 222 and other components positioned within the drive cylinder. The drive cylinder 224 has a through opening (or lumen) extending the length of the cylinder that is shaped to correspond to the flats of the nut 222 such that rotation of the drive cylinder is effective to rotate the nut and the torque shaft 110. The drive cylinder 224 can have an enlarged distal end portion 236 that can house one or more seals (e.g., O-rings 246) that form a seal with the outer surface of the main shaft 104 (FIG. 25). The handle 202 can also house a fitting 238 that has a flush port in communication with the lumen of the torque shaft 110 and/or the lumen of the main shaft 104.

The drive cylinder 224 is operatively connected to an electric motor 226 through gears 228 and 230. The handle 202 can also house a battery compartment 232 that contains batteries for powering the motor 226. Rotation of the motor 226 in one direction causes the torque shaft 110 to rotate, which in turn causes the sheath 106 to retract and uncover a prosthetic valve 10 at the distal end of the catheter assembly. Rotation of the motor 226 in the opposite direction causes the torque shaft 110 to rotate in an opposite direction, which causes the sheath 106 to move back over the prosthetic valve 10. An operator button 234 on the handle 202 allows a user to activate the motor 226, which can be rotated in either direction to un-sheath a prosthetic valve 10 or retrieve an expanded or partially expanded prosthetic valve.

As described above, the distal end portion of the nose catheter shaft 120 can be secured to an inner fork 132 that is moved relative to an outer fork 130 to release a prosthetic valve 10 secured to the end of the delivery apparatus. Movement of the shaft 120 relative to the main shaft 104 (which secures the outer fork 130) can be effected by a proximal end portion 240 of the handle 202 that is slidable relative to the main housing 244. The end portion 240 is operatively connected to the shaft 120 such that movement of the end portion 240 is effective to translate the shaft 120 axially relative to the main shaft 104 (causing a prosthetic valve 10 to be released from the inner 132 and outer 130 forks).

The end portion 240 can have flexible side panels 242 on opposite sides of the handle 202 that are normally biased outwardly in a locked position to retain the end portion relative to the main housing 244. During deployment of the prosthetic valve 10, the user can depress the side panels 242, which disengage from corresponding features in the housing 244 and allow the end portion 240 to be pulled proximally relative to the main housing, which causes corresponding axial movement of the shaft 120 relative to the main shaft. Proximal movement of the shaft 120 causes the prongs 136 of the inner fork 132 to disengage from the apertures 32 in the stent 12, which in turn allows the retaining arms 30 of the stent to deflect radially outwardly from the openings 140 in the prongs 134 of the outer fork 130, thereby releasing the prosthetic valve.

FIG. 27 shows an alternative embodiment of a motor, indicated at 400, that can be used to drive a torque shaft (e.g., torque shaft 110). In this embodiment, a catheter assembly can be connected directly to one end of a shaft 402 of the motor, without gearing. The shaft 402 includes a lumen that allows for passage of an innermost shaft (e.g., shaft 120) of the catheter assembly, a guide wire, and/or fluids for flushing the lumens of the catheter assembly.

Alternatively, the power source for rotating the torque shaft 110 can be a hydraulic power source (e.g., hydraulic pump) or pneumatic (air-operated) power source that is configured to rotate the torque shaft. In another embodiment, the handle 202 can have a manually movable lever or wheel that is operable to rotate the torque shaft 110.

In another embodiment, a power source (e.g., an electric, hydraulic, or pneumatic power source) can be operatively connected to a shaft, which is turn is connected to a prosthetic valve 10. The power source is configured to reciprocate the shaft longitudinally in the distal direction relative to a valve sheath in a precise and controlled manner in order to advance the prosthetic valve from the sheath. Alternatively, the power source can be operatively connected to the sheath in order to reciprocate the sheath longitudinally in the proximal direction relative to the prosthetic valve to deploy the prosthetic valve from the sheath.

General Considerations

For purposes of this description, certain aspects, advantages, and novel features of the embodiments of this disclosure are described herein. The disclosed methods, devices, and systems should not be construed as limiting in any way. Instead, the present disclosure is directed toward all novel and nonobvious features and aspects of the various disclosed embodiments, alone and in various combinations and subcombinations with one another. The methods, devices, and systems are not limited to any specific aspect or feature or combination thereof, nor do the disclosed embodiments require that any one or more specific advantages be present or problems be solved.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. As used herein, the terms "a", "an" and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C" or "A, B and C."

As used herein, the term "coupled" generally means physically coupled or linked and does not exclude the presence of intermediate elements between the coupled items absent specific contrary language.

In view of the many possible embodiments to which the principles of the disclosed invention may be applied, it should be recognized that the illustrated embodiments are only preferred examples of the invention and should not be taken as limiting the scope of the invention. Accordingly, the scope of the invention is defined by the following claims. We therefore claim as our invention all that comes within the scope and spirit of these claims.

We claim:

1. A delivery apparatus for delivering a medical device, comprising:
    an elongated, first component comprising an engagement portion having threads or grooves and a disengagement portion lacking the threads or grooves;
    a travelling, second component coaxially disposed relative to the first elongated component, the travelling component comprising threads or grooves configured to mate with the threads or grooves of the first elongated component; and
    a biasing member located proximate the disengagement portion of the first elongated component;
    wherein the first elongated component is configured to be rotatable relative to the traveling component such that rotation of the first elongated component causes the travelling component to move axially along the threads or grooves of the engagement portion, the threads or grooves of the travelling component disengaging from the threads or grooves of the engagement portion upon movement of the travelling component into the disengagement portion of the first elongated component, and the biasing member biasing the travelling component against the threads or grooves of the engagement portion such that the travelling component reengages the engagement portion when the rotational direction of the first elongated component is reversed.

2. The delivery apparatus of claim 1, wherein the engagement portion and the disengagement portion are formed on an inner surface of the first elongated component.

3. The delivery apparatus of claim 1, further comprising a pull wire coupled to the travelling component.

4. The delivery apparatus of claim 3, wherein the pull wire is coupled to a distal end portion of a shaft of the delivery apparatus.

5. The delivery apparatus of claim 1, wherein the biasing member comprises a spring.

6. The delivery apparatus of claim 1, wherein the engagement portion and the disengagement portion are formed on an outer surface of the first elongated component.

7. The delivery apparatus of claim 1, further comprising a delivery sheath configured to receive and retain a prosthetic valve in a compressed delivery state and coupled to the travelling component, wherein axial movement of the travelling component moves the sheath axially relative to the prosthetic valve.

8. The delivery apparatus of claim 1, wherein the travelling component is secured against rotation relative to the first elongated component upon rotation of the first elongated component.

9. The delivery apparatus of claim 1, further comprising a bushing disposed between the biasing member and an end of the first elongated component proximate the disengagement portion.

10. The delivery apparatus of claim 1, wherein the disengagement portion has a length that is at least as large as a length of a threaded or grooved portion of the travelling component.

11. The delivery apparatus of claim 1, wherein the disengagement portion has a length that is equal to or greater than the length of the travelling component.

12. The delivery apparatus of claim 1, wherein the travelling component is a nut, ring, or sheath.

13. A method comprising:
    inserting a distal end of an elongated delivery apparatus into a patient, the elongated delivery apparatus comprising an elongated component comprising an engagement portion having threads or grooves and a disengagement portion lacking the threads or grooves;
    rotating the elongated component in a first rotational direction to move a travelling component axially along the engagement portion of the elongated component in a first axial direction;
    axially moving the travelling component into the disengagement portion of the elongated component, wherein continued rotation of the elongated component in the first rotational direction does not cause the travelling component to continue to move axially in the first axial direction when the travelling component is located in the disengagement portion;
    biasing the travelling component against the engagement portion of the elongated component; and
    rotating the elongated component in a second rotational direction, wherein the biasing of the travelling component facilitates reengagement of the traveling component with the engagement portion of the elongated component and continued rotation of the elongated component in the second rotational direction moves the travelling component in a second axial direction.

14. The method of claim 13, wherein biasing the travelling component against the engagement portion of the elongated component comprises engaging the travelling component with a spring.

15. The method of claim 13, wherein rotating the elongated component deflects a portion of a distal end of the elongated delivery apparatus.

16. The method of claim 13, wherein the travelling component pulls a wire coupled to a distal portion of the elongated delivery apparatus.

17. The method of claim 13, wherein the elongated delivery apparatus comprises a delivery sheath containing a prosthetic valve in a radially compressed state and rotating the elongated component moves the delivery sheath relative to the prosthetic valve.

18. The method of claim 13, further comprising providing tactile feedback to a user when the travelling component is moved into the disengagement portion.

19. The method of claim 13, further comprising providing audible feedback to a user when the travelling component is moved into the disengagement portion.

20. The method of claim 13, further comprising compressing a biasing member with the travelling component when the travelling component is disposed within the disengagement portion.

* * * * *